United States Patent [19]

Hagen et al.

[11] Patent Number: 4,784,950

[45] Date of Patent: Nov. 15, 1988

[54] EXPRESSION OF FACTOR VII ACTIVITY IN MAMMALIAN CELLS

[75] Inventors: Frederick S. Hagen; Mark J. Murray; Sharon J. Busby; Kathleen L. Berkner, all of Seattle; Margaret Y. Insley, Woodinville; Richard G. Woodbury; Charles L. Gray, both of Seattle, all of Wash.

[73] Assignee: ZymoGenetics, Inc., Seattle, Wash.

[21] Appl. No.: 810,002

[22] Filed: Dec. 16, 1986

Related U.S. Application Data

[63] Continuation-in-part of Ser. No. 724,311, Apr. 17, 1985.

[51] Int. Cl.$^4$ ............... C12N 15/00; C12P 21/02; C07H 15/12; C07K 13/00
[52] U.S. Cl. ............... 435/68; 435/172.3; 435/240.2; 435/320; 935/11; 935/32; 935/48; 935/60; 935/70; 536/27; 530/384
[58] Field of Search ............... 536/27; 435/68, 172.3, 435/317, 240, 320; 530/384; 935/32, 47, 48, 55, 60, 70; 938/11

[56] References Cited

U.S. PATENT DOCUMENTS

| | | |
|---|---|---|
| 4,382,083 | 5/1983 | Thomas . |
| 4,456,591 | 6/1984 | Thomas . |
| 4,459,288 | 7/1984 | Thomas . |

OTHER PUBLICATIONS

Buchthal and Bell, Biochemistry 20:1077–1082, 1983.
D. S. Anson et al., "Expression of Active Human Clotting Factor IX from Recombinant DNA Clones in Mammalian Cells", Nature 315:683–685, 1985.
S. Busby et al., "Expression of Active Human Factor IX in Transfected Cells", Nature 316:271–273, 1985.
G. G. Brownlee et al., "Clotting Factor VIII Cloned", Nature 312:326–330, 1984.
J. Gitschier et al., "Characterization of the Human Factor VIII Gene", Nature 312:326–330, 1984.
W. Wood et al., "Expression of Active Human Factor VIII from Recombinant DNA Clones", Nature 312:330–337, 1984.
G. A. Vehar et al., "Structure of Human Factor VIII", Nature 312:337–342, 1984.
J. J. Toole et al., "Molecular Cloning of a cDNA Encoding Human Anti-Haemophilic Factor", Nature 312: 342–347, 1984.
W. Kisiel et al., "Enzymological Aspects of Blood Coagulation", Behring Inst. Mitt. 73:29–42, 1983.
U. Hedner et al., "Use of Human Factor VIIa in the Treatment of Two Hemophilia A Patients with High-Titer Inhibitors", J. Clin. Invest. 71:1836–1841, 1983.
B. A. McMullen et al., "The Occurrence of Beta-Hydroxyaspartic Acid in the Vitamin K-Dependent Blood Coagulation Zymogens", Biochem. Biophys. Res. Comm. 115:8–14, 1983.
M. Zur et al., "The Esterase Activity of Coagulation Factor VII", J. Biol. Chem. 253:2203–2209, 1978.
K. Kurachi et al., "Isolation and Characterization of a cDNA Coding for Human Factor IX", Proc. Natl. Acad. Sci. USA 79:6461–6464, 1982.
R. G. DiScipio et al., "A Comparison of Human Prothrombin, Factor IX (Christmas Factor), Factor X (Stuart Factor), and Protein S", Biochem. 16:698–706, 1977.
E. W. Davie et al., "Cloning of Vitamin K-Dependent Clotting Factors", in Calcium Binding Proteins, B. de Bernard et al. (ed), Elsevier Science Publishers, pp. 45–52, 1983.
L. V. M. Rao et al., "Purification of Human Factor VII Utilizing O-(Diethylaminoethyl)-Sephadex and Sulfopropyl-Sephadex Chromatography", Anal. Biochem. 136:357–361, 1984.
W. Kisiel et al., "Isolation and Characterization of Human Factor VIIa", Thromb. Res. 22:375–380, 1981.
K. Katayama et al., "Comparison of Amino Acid Sequence of Bovine Coagulation Factor IX (Christmas Factor) with that of Other Vitamin K-Dependent Plasma Proteins", Proc. Natl. Acad. Sci. USA 76:4990–4994, 1979.
E. W. Davie et al., "Basic Mechanisms in Blood Coagulation", Ann. Rev. Biochem. 44:799–824, 1975.
G. A. Vehar et al., "Bioengineering of Blood Plasma Proteins", Scand. J. Haematol. (Suppl. 40) 33:45–51, 1984.
R. Flengsrud, "Purification and Some Characteristics of the Human Coagulation Factor VII", Eur. J. Biochem. 98:455-464, 1979.
K. H. Choo et al., "Molecular Cloning of the Gene for Human Anti-Haemophilic Factor IX", Nature 299:178-180, 1982.
D. S. Anson et al., "The Gene Structure of Human Anti-Haemophilic Factor IX", EMBO J. 3:1053-1060, 1984.
G. J. Broze et al., "Purification and Properties of Human Coagulation Factor VII", J. Biol. Chem. 255:1242-1247, 1980.

*Primary Examiner*—Elizabeth Weimar
*Attorney, Agent, or Firm*—Seed and Berry

[57] ABSTRACT

Methods are disclosed for producing proteins having biological activity for blood coagulation mediated by Factor VIIa. The proteins are produced by mammalian host cells which have been stably transfected with a DNA construct containing a nucleotide sequence which codes at least partially for either Factor VII. The nucleotide sequence comprises a first nucleotide sequence encoding a calcium binding domain, joined to a second nucleotide sequence positioned downstream of the first sequence. In particular, the first nucleotide sequence may be derived from a genomic clone or cDNA clone of Factor VII. The second sequence encodes a catalytic domain for the serine protease activity of Factor VIIA. The joined sequences code for proteins having substantially the same biological activity for blood coagulation as Factor VIIa.

32 Claims, 21 Drawing Sheets

FIG. 1A

```
EcoRIa                       24                    39                    54
GAATTCCGG TGC AGG ACG AAG CTG TTC TGG ATT TCT TAC AGT GAT GGG GAC CAG
          Arg Thr Lys Leu Phe Trp Ile Ser Tyr Ser Asp Gly Asp Gln 69                  84                    99
TGT GCC TCA AGT CCA TGC CAG AAT GGG GGC TCC TGC AAG GAC CAG CTC CAG TCC
Cys Ala Ser Ser Pro Cys Gln Asn Gly Gly Ser Cys Lys Asp Gln Leu Gln Ser 114                 129                 144                 159
TAT ATC TGC TTC TGC CTC CCT GCC TTC GAG GGC CGG AAC TGT GAG ACG CAC AAG
Tyr Ile Cys Phe Cys Leu Pro Ala Phe Glu Gly Arg Asn Cys Glu Thr His Lys 174                 189                 204        Pst Ia'
GAT GAC CAG CTG ATC TGT GTG AAC GAG AAC GGC GGC TGT GAG CAG TAC TGC AGT
Asp Asp Gln Leu Ile Cys Val Asn Glu Asn Gly Gly Cys Glu Gln Tyr Cys Ser 219                 234                 249                 264
GAC CAC ACG GGC ACC AAG CGC TCC TGT CGG TGC CAC GAG GGG TAC TCT CTG CTG
Asp His Thr Gly Thr Lys Arg Ser Cys Arg Cys His Glu Gly Tyr Ser Leu Leu 279                 294                 309                 324
GCA GAC GGG GTG TCC TGC ACA CCC ACA GTT GAA TAT CCA TGT GGA AAA ATA CCT
Ala Asp Gly Val Ser Cys Thr Pro Thr Val Glu Tyr Pro Cys Gly Lys Ile Pro

Xba I       339                 354                 369
ATT CTA GAA AAA AGA AAT GCC AGC AAA CCC CAA GGC CGA ATT GTG GGG GGC AAG
Ile Leu Glu Lys Arg Asn Ala Ser Lys Pro Gln Gly Arg Ile Val Gly Gly Lys 384                 399                 414                 429
GTG TGC CCC AAA GGG GAG TGT CCA TGG CAG GTC CTG TTG TTG GTG AAT GGA GCT
Val Cys Pro Lys Gly Glu Cys Pro Trp Gln Val Leu Leu Leu Val Asn Gly Ala 444                 459                 474
CAG TTG TGT GGG GGG ACC CTG ATC AAC ACC ATC TGG GTG GTC TCC GCG GCC CAC
Gln Leu Cys Gly Gly Thr Leu Ile Asn Thr Ile Trp Val Val Ser Ala Ala His 489                 504                 519                 534
TGT TTC GAC AAA ATC AAG AAC TGG AGG AAC CTG ATC GCG GTG CTG GGC GAG CAC
Cys Phe Asp Lys Ile Lys Asn Trp Arg Asn Leu Ile Ala Val Leu Gly Glu His 549                 564                 579                 594
GAC CTC AGC GAG CAC GAC GGG GAT GAG CAG AGC CGG CGG GTG GCG CAG GTC ATC
Asp Leu Ser Glu His Asp Gly Asp Glu Gln Ser Arg Arg Val Ala Gln Val Ile

609    Sma I    624                 639
ATC CCC AGC ACG TAC GTC CCG GGC ACC ACC AAC CAC GAC ATC GCG CTC CTC CGC
Ile Pro Ser Thr Tyr Val Pro Gly Thr Thr Asn His Asp Ile Ala Leu Leu Arg 654                 669                 684                 699
CTG CAC CAG CCC GTG GTC CTC ACT GAC CAT GTG GTG CCC CTC TGC CTG CCC GAA
Leu His Gln Pro Val Val Leu Thr Asp His Val Val Pro Leu Cys Leu Pro Glu
```

```
               714                    729                      744
CGG ACG TTC TCT GAG AGG ACG CTG GCC TTC GTG CGC TTC TCA TTG GTC AGC GGC
Arg Thr Phe Ser Glu Arg Thr Leu Ala Phe Val Arg Phe Ser Leu Val Ser Gly 759                774       Nar I     789                    804
TGG GGC CAG CTG CTG GAC CGT GGC GCC ACG GCC CTG GAG CTC ATG GTC CTC AAC
Trp Gly Gln Leu Leu Asp Arg Gly Ala Thr Ala Leu Glu Leu Met Val Leu Asn 819                    834    Pst Ib   849                    864
GTG CCC CGG CTG ATG ACC CAG GAC TGC CTG CAG CAG TCA CGG AAG GTG GGA GAC
Val Pro Arg Leu Met Thr Gln Asp Cys Leu Gln Gln Ser Arg Lys Val Gly Asp 879                    894                    909
TCC CCA AAT ATC ACG GAG TAC ATG TTC TGT GCC GGC TAC TCG GAT GGC AGC AAG
Ser Pro Asn Ile Thr Glu Tyr Met Phe Cys Ala Gly Tyr Ser Asp Gly Ser Lys 924                    939                    954                    969
GAC TCC TGC AAG GGG GAC AGT GGA GGC CCA CAT GCC ACC CAC TAC CGG GGC ACG
Asp Ser Cys Lys Gly Asp Ser Gly Gly Pro His Ala Thr His Tyr Arg Gly Thr 984                    999                    1014
TGG TAC CTG ACG GGC ATC GTC AGC TGG GGC CAG GGC TGC GCA ACC GTG GGC CAC
Trp Tyr Leu Thr Gly Ile Val Ser Trp Gly Gln Gly Cys Ala Thr Val Gly His 1029                1044                  1059 TaqI         1074
TTT GGG GTG TAC ACC AGG GTC TCC CAG TAC ATC GAG TGG CTG CAA AAG CTC ATG
Phe Gly Val Tyr Thr Arg Val Ser Gln Tyr Ile Glu Trp Leu Gln Lys Leu Met 1089                 1104                 1119                    1138
CGC TCA GAG CCA CGC CCA GGA GTC CTC CTG CGA GCC CCA TTT CCC TAG CCCAGCAGCC
Arg Ser Glu Pro Arg Pro Gly Val Leu Leu Arg Ala Pro Phe Pro
                                                                        PstIc
    1148      1158       1168      1178      1188      1198      1208
CTGGCCTGTG GAGAGAAAGC CAAGGCTGCG TCGAACTGTC CTGGCACCAA ATCCCATATA TTCTTCTGCA 1218       1228       1238      1248       1258       1268       1278
GTTAATGGGG TAGAGGAGGG CATGGGAGGG AGGGAGAGGT GGGGAGGGAG ACAGAGACAG AAACAGAGAG 1288       1298       1308       1318       1328       1338       1348
AGACAGAGAC AGAGAGAGAC TGAGGGAGAG ACTCTGAGGA CCATGGACAG AGACTCAAAG AGACTCCAAG 1358       1368       1378       1388       1398       1408       1418
ATTCAAAGAG ACTAATAGAG ACACAGAGAT GGAATAGAAA AGATGAGAGG CAGAGGCAGA CAGGCGCTGG 1428       1438       1448       1458       1468       1478       1488
ACAGAGGGGC AGGGGAGTGC CAAGGTTGTC CTGGAGGCAG ACAGCCCAGC TGAGCCTCCT TACCTCCCTT
```

```
       1498       1508       1518       1528       1538       1548       1558
 CAGCCAAGCC CCACCTGCAC GTGATCTGCT GGCCCTCAGG CTGCTGCTCT GCCTTCATTG CTGGAGACAG 1568       1578       1588       1598       1608       1618       1628
 TAGAGGCATG ACACACATGG ATGCACACAC ACACACGCCA TGCACACACA CAGAGATATG CACACACACG 1638       1648       1658       1668       1678       1688       1698
 GATGCACACA CAGATGGTCA CACAGAGTAC GCAAACACAC CGATGCACAC GCACATAGAG ATATGCACAC 1708       1718       1728       1738       1748       1758       1768
 ACAGATGCAC ACACAGATAT ACACATGGAG TGCACGCACA TGCCAATGCA CGCACACATC AGTGCACACG 1778       1788       1798       1808       1818       1828       1838
 GATGCACAGA GATATGCACA CACCGATGTG CGCACACACA GATATGCACA CACATGGATG AGCACACACA 1848       1858       1868       1878       1888       1898       1908
 CACCAAGTGC GCACACACAC CGATGTACAC ACAGATGCAC ACACAGATGC ACACACACCG ATGCTGACTC 1918       1928       1938       1948       1958       1968       1978
 CATGTGTGCT GTCCTCTGAA GGCGGTTGTT TAGCTCTCAC TTTTCTGGTT CTTATCCATT ATCATCTTCA 1988       1998       2008       2018       2028       2038       2048
 CTTCAGACAA TTCAGAAGCA TCACCATGCA TGGTGGCGAA TGCCCCCAAA CTCTCCCCCA AATGTATTTC 2058       2068       2078       2088       2098       2108       2118
 TCCCTTCGCT GGGTGCCGGG CTGCACAGAC TATTCCCCAC CTGCTTCCCA GCTTCACAAT AAACGGCTGC 2128       2138       2148       2158       2168      EcoRIb
 GTCTCCTCGC AAAAAAAAAA AAAAAAAAAA AAAAAAAAAA AAAAAAAAAA AAGGAATTC
```

FIG. 1B

```
                                              -60
                                      MetValSerGlnAlaLeuArgLeuLeu
TCAACAGGCAGGGGCAGCACTGCAGAGATTTCATCATGGTCTCCCAGGCCCTCAGGCTCCTC
        10        20        30        40        50        60

-50                                   -40 ↓
CysLeuLeuLeuGlyLeuGlnGlyCysLeuAlaAlaGlyGlyValAlaLysAlaSerGlyGly
TGCCTTCTGCTTGGGCTTCAGGGCTGCCTGGCTGCAGGCGGGGTCGCTAAGGCCTCAGGAGGA
        70        80        90       100       110       120

-30                            -20        ↓
GluThrArgAspMetProTrpLysProGlyProHisArgValPheValThrGlnGluGlu
GAAACACGGGACATGCCGTGGAAGCCGGGGCCTCACAGAGTCTTCGTAACCCAGGAGGAA
       130       140       150       160       170       180

-10                         -1 +1                        +10
AlaHisGlyValLeuHisArgArgArgArgAlaAsnAlaPheLeuGluGluLeuArgPro
GCCCACGGCGTCCTGCACCGGCGCCGGCGCGCCAACGCGTTCCTGGAGGAGCTGCGGCCG
       190       200       210       220       230       240

+20                          +30
GlySerLeuGluArgGluCysLysGluGluGlnCysSerPheGluGluAlaArgGluIle
GGCTCCCTGGAGAGGGAGTGCAAGGAGGAGCAGTGCTCCTTCGAGGAGGCCCGGGAGATC
       250       260       270       280       290       300

+40                          +50
PheLysAspAlaGluArgThrLysLeuPheTrpIleSerTyrSerAspGlyAspGlnCys
TTCAAGGACGCGGAGAGGACGAAGCTGTTCTGGATTTCTTACAGTGATGGGGACCAGTGT
       310       320       330       340       350       360

+60                          +70
AlaSerSerProCysGlnAsnGlyGlySerCysLysAspGlnLeuGlnSerTyrIleCys
GCCTCAAGTCCATGCCAGAATGGGGGCTCCTGCAAGGACCAGCTCCAGTCCTATATCTGC
       370       380       390       400       410       420

+80                          +90
PheCysLeuProAlaPheGluGlyArgAsnCysGluThrHisLysAspAspGlnLeuIle
TTCTGCCTCCCTGCCTTCGAGGGCCGGAACTGTGAGACGCACAAGGATGACCAGCTGATC
       430       440       450       460       470       480

+100                        +110
CysValAsnGluAsnGlyGlyCysGluGlnTyrCysSerAspHisThrGlyThrLysArg
TGTGTGAACGAGAACGGCGGCTGTGAGCAGTACTGCAGTGACCACACGGGCACCAAGCGC
       490       500       510       520       530       540

+120                        +130
SerCysArgCysHisGluGlyTyrSerLeuLeuAlaAspGlyValSerCysThrProThr
TCCTGTCGGTGCCACGAGGGGTACTCTCTGCTGGCAGACGGGGTGTCCTGCACACCCACA
       550       560       570       580       590       600

+140                        +150
ValGluTyrProCysGlyLysIleProIleLeuGluLysArgAsnAlaSerLysProGln
GTTGAATATCCATGTGGAAAAATACCTATTCTAGAAAAAAGAAATGCCAGCAAACCCCAA
       610       620       630       640       650       660
```

```
                                        +380                              +390
    ValGlyHisPheGlyValTyrThrArgValSerGlnTyrIleGluTrpLeuGlnLysLeu
    GTGGGCCACTTTGGGGTGTACACCAGGGTCTCCCAGTACATCGAGTGGCTGCAAAAGCTC
        1330      1340      1350      1360      1370      1380

+400              +406
    MetArgSerGluProArgProGlyValLeuLeuArgAlaProPhePro***
    ATGCGCTCAGAGCCACGCCCAGGAGTCCTCCTGCGAGCCCCATTTCCCTAGCCCAGCAGC
        1390      1400      1410      1420      1430      1440

CCTGGCCTGTGGAGAGAAAGCCAAGGCTGCGTCGAACTGTCCTGGCACCAAATCCCATAT
        1450      1460      1470      1480      1490      1500

ATTCTTCTGCAGTTAATGGGGTAGAGGAGGGCATGGGAGGGAGGGAGAGGTGGGGAGGGA
        1510      1520      1530      1540      1550      1560

GACAGAGACAGAAACAGAGAGAGACAGAGACAGAGAGAGACTGAGGGAGAGACTCTGAGG
        1570      1580      1590      1600      1610      1620

ACATGGAGAGAGACTCAAAGAGACTCCAAGATTCAAAGAGACTAATAGAGACACAGAGAT
        1630      1640      1650      1660      1670      1680

GGAATAGAAAAGATGAGAGGCAGAGGCAGACAGGCGCTGGACAGAGGGGCAGGGGAGTGC
        1690      1700      1710      1720      1730      1740

CAAGGTTGTCCTGGAGGCAGACAGCCCAGCTGAGCCTCCTTACCTCCCTTCAGCCAAGCC
        1750      1760      1770      1780      1790      1800

CCACCTGCACGTGATCTGCTGGCCCTCAGGCTGCTGCTCTGCCTTCATTGCTGGAGACAG
        1810      1820      1830      1840      1850      1860

TAGAGGCATGAACACACATGGATGCACACACACACACGCCAATGCACACACACAGAGATA
        1870      1880      1890      1900      1910      1920

TGCACACACACGGATGCACACACAGATGGTCACACAGAGATACGCAAACACACCGATGCA
        1930      1940      1950      1960      1970      1980

CACGCACATAGAGATATGCACACACAGATGCACACACAGATATACACATGGATGCACGCA
        1990      2000      2010      2020      2030      2040

CATGCCAATGCACGCACACATCAGTGCACACGGATGCACAGAGATATGCACACACCGATG
        2050      2060      2070      2080      2090      2100

TGCGCACACACAGATATGCACACACATGGATGAGCACACACACACCAAGTGCGCACACAC
        2110      2120      2130      2140      2150      2160

ACCGATGTACACACACAGATGCACACACAGATGCACACACACCGATGCTGACTCCATGTG
        2170      2180      2190      2200      2210      2220

TGCTGTCCTCTGAAGGCGGTTGTTTAGCTCTCACTTTTCTGGTTCTTATCCATTATCATC
        2230      2240      2250      2260      2270      2280

TTCACTTCAGACAATTCAGAAGCATCACCATGCATGGTGGCGAATGCCCCCAAACTCTCC
        2290      2300      2310      2320      2330      2340

CCCAAATGTATTTCTCCCTTCGCTGGGTGCCGGGCTGCACAGACTATTCCCCACCTGCTT
        2350      2360      2370      2380      2390      2400
```

```
                                    +160                                    +170
    GlyArgIleValGlyGlyLysValCysProLysGlyGluCysProTrpGlnValLeuLeu
    GGCCGAATTGTGGGGGGCAAGGTGTGCCCCAAAGGGGAGTGTCCATGGCAGGTCCTGTTG
       670       680       690       700       710       720

+180                                    +190
    LeuValAsnGlyAlaGlnLeuCysGlyGlyThrLeuIleAsnThrIleTrpValValSer
    TTGGTGAATGGAGCTCAGTTGTGTGGGGGGACCCTGATCAACACCATCTGGGTGGTCTCC
       730       740       750       760       770       780

+200                                    +210
    AlaAlaHisCysPheAspLysIleLysAsnTrpArgAsnLeuIleAlaValLeuGlyGlu
    GCGGCCCACTGTTTCGACAAAATCAAGAACTGGAGGAACCTGATCGCGGTGCTGGGCGAG
       790       880       810       820       830       840

+220                                    +230
    HisAspLeuSerGluHisAspGlyAspGluGlnSerArgArgValAlaGlnValIleIle
    CACGACCTCAGCGAGCACGACGGGGATGAGCAGAGCCGGCGGGTGGCGCAGGTCATCATC
       850       860       870       880       890       900

+240                                    +250
    ProSerThrTyrValProGlyThrThrAsnHisAspIleAlaLeuLeuArgLeuHisGln
    CCCAGCACGTACGTCCCGGGCACCACCAACCACGACATCGCGCTGCTCCGCCTGCACCAG
       910       920       930       940       950       960

+260                                    +270
    ProValValLeuThrAspHisValValProLeuCysLeuProGluArgThrPheSerGlu
    CCCGTGGTCCTCACTGACCATGTGGTGCCCCTCTGCCTGCCCGAACGGACGTTCTCTGAG
       970       980       990      1000      1010      1020

+280                                    +290
    ArgThrLeuAlaPheValArgPheSerLeuValSerGlyTrpGlyGlnLeuLeuAspArg
    AGGACGCTGGCCTTCGTGCGCTTCTCATTGGTCAGCGGCTGGGGCCAGCTGCTGGACCGT
      1030      1040      1050      1060      1070      1080

+300                                    +310
    GlyAlaThrAlaLeuGluLeuMetValLeuAsnValProArgLeuMetThrGlnAspCys
    GGCGCCACGGCCCTGGAGCTCATGGTCCTCAACGTGCCCCGGCTGATGACCCAGGACTGC
      1090      1100      1110      1120      1130      1140

+320                                    +330
    LeuGlnGlnSerArgLysValGlyAspSerProAsnIleThrGluTyrMetPheCysAla
    CTGCAGCAGTCACGGAAGGTGGGAGACTCCCCAAATATCACGGAGTACATGTTCTGTGCC
      1150      1160      1170      1180      1190      1200

+340                                    +350
    GlyTyrSerAspGlySerLysAspSerCysLysGlyAspSerGlyGlyProHisAlaThr
    GGCTACTCGGATGGCAGCAAGGACTCCTGCAAGGGGGACAGTGGAGGCCCACATGCCACC
      1210      1220      1230      1240      1250      1260

+360                                    +370
    HisTyrArgGlyThrTrpTyrLeuThrGlyIleValSerTrpGlyGlnGlyCysAlaThr
    CACTACCGGGGCACGTGGTACCTGACGGGCATCGTCAGCTGGGGCCAGGGCTGCGCAACC
      1270      1280      1290      1300      1310      1320
```

```
CCCAGCTTCACAATAAACGGCTGCGTCTCCTCCGCACACCTGTGGTGCCTGCCACCCAAA
 2410     2420      2430      2240     2450      2460

AAAAAAAAAAAAAAAAAA
 2470     2480
```

FIG. 2A

|              |   | 1 |   |   |   |   |   |   |   |   | 10 |   |   |   |   |   |   |   |   |   | 20 |   |   |   |   |   |   |   |   |   | 30 |   |   |   |   |   |   |   |   |   | 40 |
|--------------|---|---|---|---|---|---|---|---|---|---|----|---|---|---|---|---|---|---|---|---|----|---|---|---|---|---|---|---|---|---|----|---|---|---|---|---|---|---|---|---|----|
|              |   |   |   |   |   |   |   |   |   |   |    |   |   |   |   |   |   |   |   |   |    | * | * |   |   |   |   |   |   |   | *  |   |   |   |   |   | * | * |   |   |    |
| FACTOR VII   | A | N | A | - | F | L | Y | Y | L | R | P  | G | S | L | Y | R | Y | C | K | Y | Y  | Q | C | S | F | Y | Y | A | R | Y | I  | F | Y | K | X | R | T | K | L |   |    |
| FACTOR IX    | Y | N | S | G | K | L | Y | Y | F | V | Q  | G | N | L | Y | R | Y | C | M | Y | Y  | K | C | S | F | Y | Y | A | R | Y | V  | F | Y | N | T | Y | R | T | T | Y |    |
| FACTOR X     | A | N | S | - | F | L | Y | Y | M | K | K  | G | H | L | Y | R | Y | C | M | Y | T  | T | C | S | Y | Y | Y | A | R | Y | V  | F | Y | D | S | D | K | T | N | Y |    |
| PROTEIN C    | A | N | S | - | F | L | Y | Y | L | R | H  | S | S | L | Y | R | Y | C | I | Y | Y  | I | C | D | F | Y | Y | A | L | Y | I  | F | Q | N | V | D | D | T | L | A |    |
| PROTHROMBIN  | A | N | T | - | F | L | Y | Y | V | R | K  | G | N | L | Y | R | Y | C | V | Y | T  | T | C | S | Y | Y | Y | A | F | Y | A  | L | Y | S | S | T | A | T | D | V |    |

|              |   |   |   |   | 50 |   |   |   |   |   |   |   |   |   | 60 |   |   |   |   |   |   |   |   |   | 70 |
|--------------|---|---|---|---|----|---|---|---|---|---|---|---|---|---|----|---|---|---|---|---|---|---|---|---|----|
| FACTOR VII   | F | W | I | S | Y  | S | D | G | D | Q | C | A | S | S | -  | - | - | - | - | P | C | Q | N | G | G  | S | C | K | D | Q | L | Q | S | Y | I | C | F |
| FACTOR IX    | F | W | K | Q | Y  | V | D | G | D | Q | C | E | S | N | -  | - | - | - | - | P | C | L | N | G | G  | S | C | K | B | D | I | N | S | T | E | C | W |
| FACTOR X     | F | W | N | K | Y  | K | D | G | D | Q | C | E | T | S | -  | - | - | - | - | P | C | Q | N | Q | G  | K | C | K | B | G | L | G | E | Y | T | C | T |
| PROTEIN C    | F | W | S | K | H  | V | D | G | D | Q | C | L | V | L | P  | L | E | H | P | C | A | S | L | C | C  | G | H | G | T | C | I | B | G | I | G | S | F | S | C | D |
| PROTHROMBIN  | F | W | A | K | Y  | T | A | C | E | T | A | R | T | P | R  | D | K | L | A | A | C | L | E | G | N  | C | A | E | G | L | G | T | N | Y | R | G | H | V | N | I |

|              |   |   |   |   | 80 |   |   |   |   |   |   |   |   |   | 90 |   |   |   |   |   |   |   |   |   | 100 |   |   |   |   |   |   |   |   |   | 110 |
|--------------|---|---|---|---|----|---|---|---|---|---|---|---|---|---|----|---|---|---|---|---|---|---|---|---|-----|---|---|---|---|---|---|---|---|---|-----|
| FACTOR VII   | C | L | P | A | F  | E | G | R | N | C | E | T | H | K | D  | D | Q | L | I | C | V | N | E | N | G   | G | C | E | Q | Y | C | S | D | H | T | G | T | K | R | S | C |
| FACTOR IX    | C | P | F | G | F  | E | G | K | N | C | E | L | D | V | T  | - | - | - | - | C | N | I | K | N | G   | R | C | E | Q | F | C | K | N | S | A | D | N | K | V | V | C |
| FACTOR X     | C | L | E | G | F  | E | G | K | N | C | E | L | F | T | R  | K | L | - | - | C | S | L | D | N | G   | D | C | D | Q | F | C | H | E | E | Q | N | S | - | V | V | C |
| PROTEIN C    | C | R | S | G | W  | E | G | R | F | C | Q | R | E | V | S  | F | L | N | - | C | S | L | D | N | G   | G | C | T | H | Y | C | L | E | E | V | G | W | - | R | R | C |
| PROTHROMBIN  | T | R | S | G | I  | E | C | Q | L | W | R | S | R | Y | P  | H | K | P | - | E | I | N | S | T | T   | H | P | G | A | D | L | Q | E | N | F | C | R | N | P | D | S |

|              |   |   |   |   | 120 |   |   |   |   |   |   |   |   |   | 130 |   |   |   |   |   |   |   |   |   | 140 |
|--------------|---|---|---|---|-----|---|---|---|---|---|---|---|---|---|-----|---|---|---|---|---|---|---|---|---|-----|
| FACTOR VII   | R | C | H | E | G   | Y | S | L | L | A | D | G | V | S | C   | T | P | T | V | E | Y | P | C | G | K   | I | P | I | L | E | K | R | N | A | S | K | P | Q | G | R |
| FACTOR IX    | S | C | T | E | G   | Y | R | L | A | G | N | Q | K | S | C   | E | P | A | V | P | F | P | C | G | R   | V | S | V | S | Q | T | S | K | L | R | T |
| FACTOR X     | S | C | A | R | G   | Y | T | L | A | D | N | G | K | A | C   | I | P | T | G | P | Y | P | C | G | K   | Q | T | L | E | R |
| PROTEIN C    | S | C | A | P | G   | Y | K | L | G | D | D | L | L | Q | C   | H | P | A | V | K | F | P | C | G | R   | P | W | K | R | M | E | K | K | R | S | H | L |
| PROTHROMBIN  | S | N | T | G | P   | W | C | Y | T | T | D | P | T | V | R   | R | Q | E | C | S | I | P | V | C | G   | Q | D | Q | V | T | V | A | M | T | P | R | S |

FIG. 2B

```
                    1                    10                    20                    30      36
From cDNA           X X X X X X X X X X X X X X X X X X X X X X X X X X X X X X X X X X R T
                                                    *  *              *     *           *  *
Amino Acid Sequence A N A F L Y Y L R P G S L Y R Y C K Y Y Q C S F Y Y A R Y I F Y X X X X 40                   50                    60                    70
cDNA                K L F W I S Y S D G D Q C A S S P C Q N G G S C K D Q L Q S Y I C F C L
Amino Acid Sequence   L F W I S Y S D G D Q C A S S P C Q N G G S C K D Q L Q     I C F C L 80                   90                    100
cDNA                P A F E G R N C E T H K D D Q L I C V N E N G G C E Q Y C S D H T G T K
Amino Acid Sequence P A F E G R N C E T H K D D Q L                       C S D H T G T 110                  120                   130                   140
cDNA                R S C R C H E G Y S L L A D G V S C T P T V E Y P C G K I P I L E K R N
Amino Acid Sequence   S C R C H E G Y S L L A D G V S C T P T V E Y                 E K R ( )

150
cDNA                A S K P Q G R
Amino Acid Sequence A S K P Q G R
```

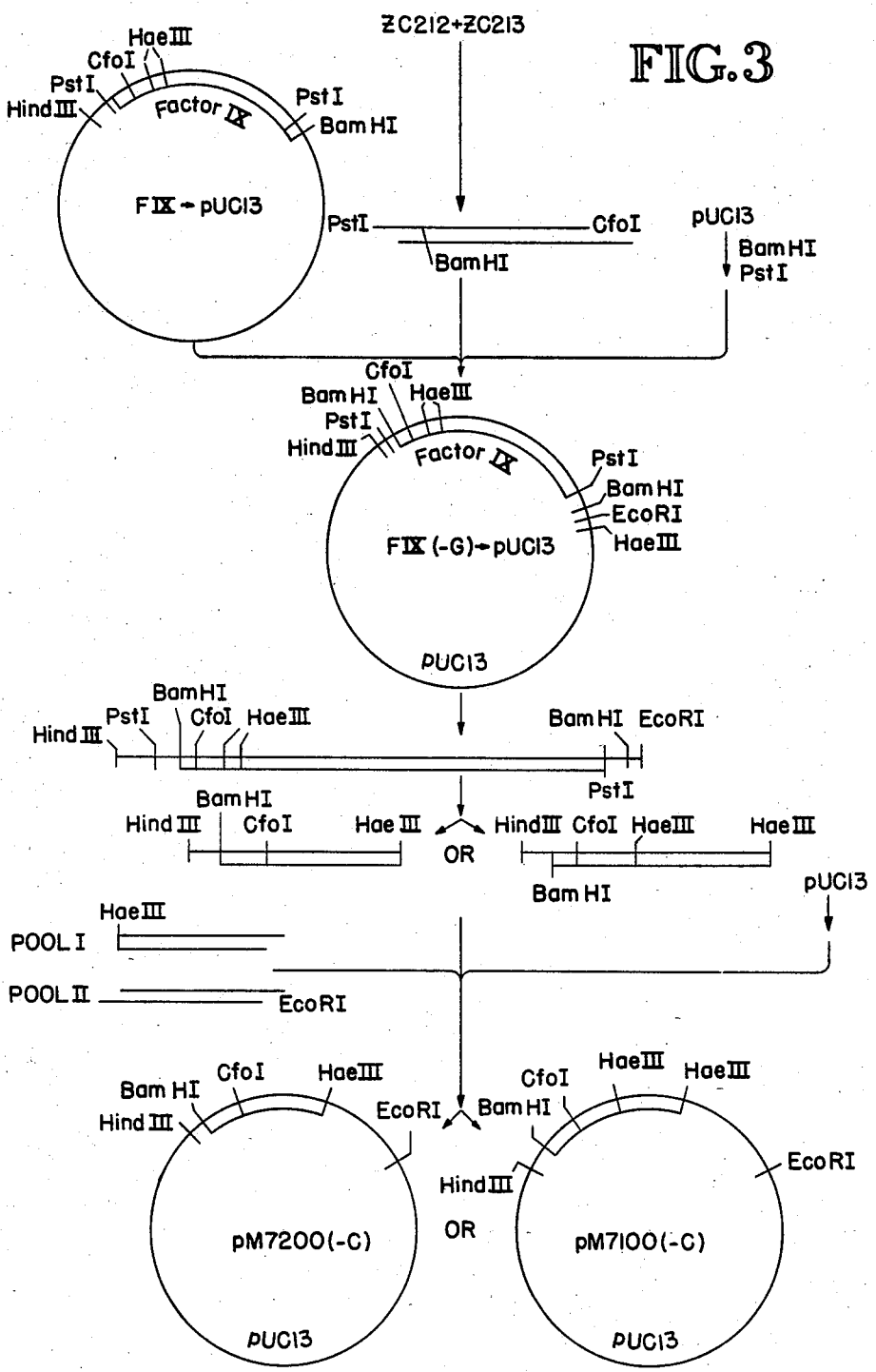

FIG. 7

```
                              21                        36
GGATCC ATG CAG CGC GTG AAC ATG ATC ATG GCA GAA TCA CCA GGC
       MET Gln Arg Val Asn MET Ile MET Ala Glu Ser Pro Gly 66                        81
CTC ATC ACC ATC TGC CTT TTA GGA TAT CTA CTC AGT GCT GAA TGT
Leu Ile Thr Ile Cys Leu Leu Gly Tyr Leu Leu Ser Ala Glu Cys 96                       111                      126
ACA GTT TTT CTT GAT CAT GAA AAC GCC AAC AAA ATT CTG AAT CGG
Thr Val Phe Leu Asp His Glu Asn Ala Asn Lys Ile Leu Asn Arg 141                      156                      171
CCA AAG AGG TAT AAT TCA GGT AAA TTG GAA GAG TTT GTT CAA GGG
Pro Lys Arg Tyr Asn Ser Gly Lys Leu Glu Glu Phe Val Gln Gly 186                      201                      216
AAC CTT GAG AGA GAA TGT ATG GAA GAA AAG TGT AGT TTT GAA GAA
Asn Leu Glu Arg Glu Cys MET Glu Glu Lys Cys Ser Phe Glu Glu 231                      246                      261
GCA CGA GAA GTT TTT GAA AAC ACT GAA AGA ACA AAG CTG TTC TGG
Ala Arg Glu Val Phe Glu Asn Thr Glu Arg Thr Lys Leu Phe Trp 276                      291                      306
ATT TCT TAC AGT GAT GGG GAC CAG TGT GCC TCA AGT CCA TGC CAG
Ile Ser Tyr Ser Asp Gly Asp Gln Cys Ala Ser Ser Pro Cys Gln 321                      336                      351
AAT GGG GGC TCC TGC AAG GAC CAG CTC CAG TCC TAT ATC TGC TTC
Asn Gly Gly Ser Cys Lys Asp Gln Leu Gln Ser Tyr Ile Cys Phe 366                      381                      396
TGC CTC CCT GCC TTC GAG GGC CGG AAC TGT GAG ACG CAC AAG GAT
Cys Leu Pro Ala Phe Glu Gly Arg Asn Cys Glu Thr His Lys Asp 411                      426                      441
GAC CAG CTG ATC TGT GTG AAC GAG AAC GGC GGC TGT GAG CAG TAC
Asp Gln Leu Ile Cys Val Asn Glu Asn Gly Gly Cys Glu Gln Tyr 456                      471                      486
TGC AGT GAC CAC ACG GGC ACC AAG CGC TCC TGT CGG TGC CAC GAG
Cys Ser Asp His Thr Gly Thr Lys Arg Ser Cys Arg Cys His Glu 501                      516                      531
GGG TAC TCT CTG CTG GCA GAC GGG GTG TCC TGC ACA CCC ACA GTT
Gly Tyr Ser Leu Leu Ala Asp Gly Val Ser Cys Thr Pro Thr Val 546                      561                      576
GAA TAT CCA TCT GGA AAA ATA CCT ATT CTA GAA AAA AGA AAT GCC
Glu Tyr Pro Cys Gly Lys Ile Pro Ile Leu Glu Lys Arg Asn Ala 591                      606                      621
AGC AAA CCC CAA GGC CGA ATT GTG GGG GGC AAG GTG TGC CCC AAA
Ser Lys Pro Gln Gly Arg Ile Val Gly Gly Lys Val Cys Pro Lys
```

```
      636                    651                      666
GGG GAG TGT CCA TGG CAG GTC CTG TTG TTG GTG AAT GGA GCT CAG
Gly Glu Cys Pro Trp Gln Val Leu Leu Leu Val Asn Gly Ala Gln 681                    696                      711
TTG TGT GGG GGG ACC CTG ATC AAC ACC ATC TGG GTG GTC TCC GCG
Leu Cys Gly Gly Thr Leu Ile Asn Thr Ile Trp Val Val Ser Ala 726                    741                      756
GCC CAC TGT TTC GAC AAA ATC AAG AAC TGG AGG AAC CTG ATC GCG
Ala His Cys Phe Asp Lys Ile Lys Asn Trp Arg Asn Leu Ile Ala 771                    786                      801
GTG CTG GGC GAG CAC GAC CTC AGC GAG CAC GAC GGG GAT GAG CAG
Val Leu Gly Glu His Asp Leu Ser Glu His Asp Gly Asp Glu Gln 816                    831                      846
AGC CGG CGG GTG GCG CAG GTC ATC ATC CCC AGC ACG TAC GTC CCG
Ser Arg Arg Val Ala Gln Val Ile Ile Pro Ser Thr Tyr Val Pro 861                    876                      891
GGC ACC ACC AAC CAC GAC ATC GCG CTG CTC CGC CTG CAC CAG CCC
Gly Thr Thr Asn His Asp Ile Ala Leu Leu Arg Leu His Gln Pro 906                    921                      936
GTG GTC CTC ACT GAC CAT GTG GTG CCC CTC TGC CTG CCC GAA CGG
Val Val Leu Thr Asp His Val Val Pro Leu Cys Leu Pro Glu Arg 951                    966                      981
ACG TTC TCT GAG AGG ACG CTG GCC TTC GTG CGC TTC TCA TTG GTC
Thr Phe Ser Glu Arg Thr Leu Ala Phe Val Arg Phe Ser Leu Val 996                    1011                     1026
AGC GGC TGG GGC CAG CTG CTG GAC CGT GGC GCC ACG GCC CTG GAG
Ser Gly Trp Gly Gln Leu Leu Asp Arg Gly Ala Thr Ala Leu Glu 1041                   1056                     1071
CTC ATG GTC CTC AAC GTG CCC CGG CTG ATG ACC CAG GAC TGC CTG
Leu MET Val Leu Asn Val Pro Arg Leu MET Thr Gln Asp Cys Leu 1086                   1101                     1116
CAG CAG TCA CGG AAG GTG GGA GAC TCC CCA AAT ATC ACG GAG TAC
Gln Gln Ser Arg Lys Val Gly Asp Ser Pro Asn Ile Thr Glu Tyr 1131                   1146                     1161
ATG TTC TGT GCC GGC TAC TCG GAT GGC AGC AAG GAC TCC TGC AAG
MET Phe Cys Ala Gly Tyr Ser Asp Gly Ser Lys Asp Ser Cys Lys 1176                   1191                     1206
GGG GAC AGT GGA GGC CCA CAT GCC ACC CAC TAC CGG GGC ACG TGG
Gly Asp Ser Gly Gly Pro His Ala Thr His Tyr Arg Gly Thr Trp 1221                   1236                     1251
TAC CTG ACG GGC ATC GTC AGC TGG GGC CAG GGC TGC GCA ACC GTG
Tyr Leu Thr gly Ile Val Ser Trp Gly Gln Gly Cys Ala Thr Val
```

```
      1266                    1281                   1296
GGC CAC TTT GGG GTG TAC ACC AGG GTC TCC CAG TAC ATC GAG TGG
Gly his Phe Gly Val Tyr Thr Arg Val Ser Gln Tyr Ile Glu Trp 1311                    1326                   1341
CTG CAA AAG CTC ATG CGC TCA GAG CCA CGC CCA GGA GTC CTC CTG
Leu Gln Lys Leu MET Arg Ser Glu Pro Arg Pro Gly Val Leu Leu 1356                          1378        1388        1398
CGA GCC CCA TTT CCC TAG CCCAGCAGCC CTGGCCTGTG GAGAGAAAGC
Arg Ala Pro Phe Pro 1408        1418       1428       1438        1448
CAAGGCTGCG TCGAACTGTC CTGGCACCAA ATCCCATATA TTCTTCTGCA 1458        1468       1478       1488        1498
GTTAATGGGG TAGAGGAGGG CATGGGAGGG AGGGAGAGGT GGGGAGGGAG 1508        1518       1528       1538        1548
ACAGAGACAG AAACAGAGAG AGACAGAGAC AGAGAGAGAC TGAGGGAGAG 1558        1568       1578       1588        1598
ACTCTGAGGA CCATGGAGAG AGACTCAAAG AGACTCCAAG ATTCAAAGAG 1608        1618       1628       1638        1648
ACTAATAGAG ACACAGAGAT GGAATAGAAA AGATGAGAGG CAGAGGCAGA 1658        1668       1678       1688        1698
CAGGCGCTGG ACAGAGGGGC AGGGGAGTGC CAAGGTTGTC CTGGAGGCAG 1708        1718       1728       1738        1748
ACAGCCCAGC TGAGCCTCCT TACCTCCCTT CAGCCAAGCC CCACCTGCAC 1758        1768       1778       1788        1798
GTGATCTGCT GGCCCTCAGG CTGCTGCTCT GCCTTCATTG CTGGAGACAG 1808        1818       1828       1838        1848
TAGAGGCATG ACACACATGG ATGCACACAC ACACACGCCA TGCACACACA 1858        1868       1878       1888        1898
CAGAGATATG CACACACACG GATGCACACA CAGATGGTCA CACAGAGTAC 1908        1918       1928       1938        1948
GCAAACACAC CGATGCACAC GCACATAGAG ATATGCACAC ACAGATGCAC
```

|      1958 |      1968 |      1978 |      1988 |      1998 |
ACACAGATAT ACACATGGAG TGCACGCACA TGCCAATGCA CGCACACATC

|      2008 |      2018 |      2028 |      2038 |      2048 |
AGTGCACACG GATGCACAGA GATATGCACA CACCGATGTG CGCACACACA

|      2058 |      2068 |      2078 |      2088 |      2098 |
GATATGCACA CACATGGATG AGCACACACA CACCAAGTGC GCACACACAC

|      2108 |      2118 |      2128 |      2138 |      2148 |
CGATGTACAC ACAGATGCAC ACACAGATGC ACACACACCG ATGCTGACTC

|      2158 |      2168 |      2178 |      2188 |      2198 |
CATGTGTGCT GTCCTCTGAA GGCGGTTGTT TAGCTCTCAC TTTTCTGGTT

|      2208 |      2218 |      2228 |      2238 |      2248 |
CTTATCCATT ATCATCTTCA CTTCAGACAA TTCAGAAGCA TCACCATGCA

|      2258 |      2268 |      2278 |      2288 |      2298 |
TGGTGGCGAA TGCCCCCAAA CTCTCCCCCA AATGTATTTC TCCCTTCGC1

|      2308 |      2318 |      2328 |      2338 |      2348 |
GGGTGCCGGG CTGCACAGAC TATTCCCCAC CTGCTTCCCA GCTTCACAAT

|      2358 |      2368 |      2378 |      2388 |      2398 |
AAACGGCTGC GTCTCCTCGC AAAAAAAAAA AAAAAAAAAA AAAAAAAAAA

|      2408 |      2418 |      2428 |      2438 |
AAAAAAAAAA AAGGAATTCG AGCTCGGTAC CCGGGGATCC

EXPRESSION OF FACTOR VII ACTIVITY IN MAMMALIAN CELLS

CROSS-REFERENCE TO RELATED APPLICATION

This application is a continuation-in-part of U.S. patent application Ser. No. 724,311, filed Apr. 17, 1985, pending.

DESCRIPTION

1. Technical Field

The present invention relates to blood coagulation factors in general, and more specifically, to the expression of proteins having biological activity for blood coagulation.

2. Background Art

Blood coagulation is a process consisting of a complex interaction of various blood components or factors which eventually gives rise to a fibrin clot. Generally, the blood components which participate in what has been referred to as the coagulation "cascade" are proenzymes or zymogens, enzymatically inactive proteins which are converted to proteolytic enzymes by the action of an activator, itself an activated clotting factor. Coagulation factors which have undergone such a conversion are generally referred to as "activated factors," and are designated by the addition of a lower case postscript "a" (e.g., VIIa).

There are two separate systems which can promote blood clotting and thereby participate in normal haemostasis. These systems have been referred to as the intrinsic and the extrinsic coagulation pathways. The intrinsic pathway refers to those reactions which lead to thrombin formation through utilization of factors present only in plasma. An intermediate event in the intrinsic pathway is the activation of Factor IX to Factor IXa, a reaction catalyzed by Factor XIa and calcium ions. Factor IXa then participates in the activation of Factor X in the presence of Factor VIIIa, phospholipid and calcium ions. The extrinsic pathway involves plasma factors as well as components present in tissue extracts. Factor VII, one of the proenzymes referred to above, participates in the extrinsic pathway of blood coagulation by converting (upon its activation to VIIa) Factor X to Xa in the presence of tissue factor and calcium ions. Factor Xa in turn then converts prothrombin to thrombin in the presence of Factor Va, calcium ions and phospholipid. Because the activation of Factor X to Factor Xa is an event shared by both the intrinsic and extrinsic pathways, Factor VIIa can be used for the treatment of patients with deficiencies or inhibitors of Factor VIII (Thomas, U.S. Pat. No. 4,382,083). There is also some evidence to suggest that Factor VIIa may participate in the intrinsic pathway as well (Zur and Nemerson, *J. Biol. Chem.* 253: 2203–2209, 1978) by playing a role in the activation of Factor IX.

Experimental analysis has revealed that human Factor VII is a single-chain glycoprotein with a molecular weight of approximately 50,000 daltons. In this form, the factor circulates in the blood as an inactive zymogen. Activation of Factor VII to VIIa may be catalyzed by several different plasma proteases, such as Factor XIIa. Activation of Factor VII results in the formation of two polypeptide chains, a heavy chain ($M_r = 28,000$) and a light chain ($M_r = 17,000$), held together by at least one disulfide bond. Factor VII may also be activated to VIIa in vitro, for example, by the method disclosed by Thomas in U.S. Pat. No. 4,456,591.

Factor IX circulates in the blood as a single-chain precursor of molecular weight 57,000 and is converted to an active serine protease (Factor IXa) upon cleavage by Factor XIa in the presence of Factor VIII. Factor IXa consists of a light chain and a heavy chain of molecular weights 16,000 and 29,000, respectively.

Current treatment practices for patients having coagulation disorders (e.g., deficiencies of Factor VIII and IX) generally involve replacement therapy with cryoprecipitate or other fractions of human plasma containing enriched levels of a particular factor. These preparations have heretofore been obtained from pooled human plasma, although the preparation of cryoprecipitates requires the use of a relatively large amount of human plasma as starting material.

Therapeutic uses of Factor VII exist in the treatment of individuals exhibiting a deficiency in Factor VII, as well as Factor VIII and Factor IX deficient populations, and individuals with Von Willebrand's disease. More specifically, individuals receiving Factors VIII and IX in replacement therapy frequently develop antibodies to these proteins. Continuing treatment is exceedingly difficult because of the presence of these antibodies. Patients experiencing this problem are normally treated with an activated prothrombin complex known to consist of a mixture of active and inactive clotting enzymes, including Factor VIIa. Further, recent studies indicate that small amounts (40–50 micrograms) of injected Factor VIIa are effective in controlling serious on-going bleeding episodes in Factor VIII deficient patients who have high levels of antibody in their blood (Hedner and Kisiel, *J. Clin. Invest.* 71: 1836–1841, 1983).

Due to the diverse sources of the plasma used in the preparation of cryoprecipitates, it is difficult to test the preparations to ensure that they are free of viral contamination. For instance, essentially all recipients of cryoprecipitate show a positive test for hepatitis. Recent reports have also indicated that some hemophiliacs receiving cryoprecipitate have developed acquired immune deficiency syndrome (AIDS). In addition, the purification of large amounts of these factors is extremely difficult and expensive.

Consequently, there exists a need in the art for a method of producing relatively large quantities of pure preparations of Factors VIIa and Factor IX. The present invention fulfills this need through the use of recombinant DNA technology, successfully eliminating the problem of viral contamination and, at the same time, providing a consistent and homogeneous source of active Factor VIIa to treat Factor VIII and Factor IX deficient patients and individuals with Von Willebrand's disease, as well as providing a source of purified Factor IX for use in replacement therapy.

DISCLOSURE OF THE INVENTION

Briefly stated, the present invention discloses a DNA construct containing a nucleotide sequence which codes at least partially for Factor VII. The nucleotide sequence comprises a first nucleotide sequence encoding a calcium binding domain joined to a second nucleotide sequence positioned downstream of the first sequence. The second nucleotide sequence encodes a catalytic domain for the serine protease activity of Factor VIIa. The joined sequences code for a protein which upon activation has substantially the same biological activity for blood coagulation as Factor VIIa. The first nucleotide sequence may be substantially that of a gene encoding Factor VII, Factor IX, Factor X, Protein C, prothrombin, or Protein S. Further, the first nucleotide sequence may also encode a leader peptide corresponding to the respective gene.

In particular, the first nucleotide sequence may be derived from a genomic clone or cDNA clone of Factor VII, and may encode the leader peptide and amino-terminal portion of Factor VII. The first nucleotide sequence may also include a double-stranded oligonucleotide. A particularly preferred first nucleotide sequence is that encoding the leader peptide and amino-terminal portion of Factor IX.

In addition, the present invention discloses recombinant plasmids capable of integration in mammalian host cell DNA. One of the plasmids includes a promoter followed downstream by a set of RNA splice sites, the RNA splice sites being followed downstream by a nucleotide sequence which codes at least partially for Factor VII. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor VIIa. The joined sequences code for a protein which upon activation has substantially the same biological activity for blood coagulation as Factor VIIa. The nucleotide sequence is then followed downstream by a polyadenylation signal.

Similar to the recombinant plasmid noted above, the present invention also discloses a second plasmid which includes a promoter followed downstream by a set of RNA splice sites, the RNA splice sites being followed downstream by a nucleotide sequence which codes at least partially for Factor IX. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor IX. The joined sequences code for a protein having substantially the same biological activity for blood coagulation as Factor IX. The nucleotide sequence is then followed downstream by a polyadenylation signal.

A third aspect of the invention discloses mammalian cells stably transfected to produce a protein having substantially the same biological activity, upon activation, as Factor VIIa. The cells are transfected with a DNA construct containing a nucleotide sequence which at least partially codes for Factor VII. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor VIIa. The joined sequences code for a protein which, upon activation, has substantially the same biological activity for blood coagulation as Factor VIIa.

An additional aspect of the invention discloses mammalian cells stably transfected to produce a protein having substantially the same biological activity as Factor IX. The cells are transfected with a DNA construct containing a nucleotide sequence which codes at least partially for Factor IX. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor IX. The joined sequences code for a protein having substantially the same biological activity for blood coagulation as Factor IX.

The present invention further provides for a method of producing a protein having biological activity for blood coagulation mediated by Factor VIIa through establishing a mammalian host cell which contains a DNA construct containing a nucleotide sequence which codes at least partially for Factor VII. The nucleotide sequence comprises a first nucleotide sequence which encodes a calcium binding domain joined to a second nucleotide sequence positioned downstream of the first sequence. The second sequence encodes a catalytic domain for the serine protease activity of Factor VIIa. The joined sequences code for a protein which, upon activation, has substantially the same biological activity for blood coagulation as Factor VIIa. Subsequently, the mammalian host is grown in an appropriate medium and the protein product encoded by the DNA construct and produced by the mammalian host cell is isolated. The protein product is then activated to generate Factor VIIa.

Still a further aspect of the present invention discloses a method of producing a protein having biological activity for blood coagulation mediated by Factor IX. The method comprises establishing a mammalian host cell which contains a DNA construct containing a nucleotide sequence which codes at least partially for Factor IX. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor IX. The joined sequences code for a protein having substantially the same biological activity for blood coagulation as Factor IX. The mammalian host cell is subsequently grown in an appropriate medium and the protein product encoded by the mammalian host cell is isolated. Protein products produced by the methods noted above are also disclosed.

Yet another aspect of the present invention discloses a DNA construct comprising a DNA sequence encoding Factor VII. In a preferred embodiment, the DNA sequence comprises the cDNA sequence of FIG. 1*b* from bp 36 to bp 1433. In another preferred embodiment, the DNA sequence comprises the cDNA sequence of FIG. 1*b* from bp 36 to bp 99, followed downstream by the sequence from bp 166 to bp 1433. Recombinant plasmids capable of integration in mammalian host cell DNA comprising the DNA sequences described immediately above are also disclosed.

Mammalian cells stably transfected with a recombinant plasmid comprising a DNA sequence encoding Factor VII are also disclosed. In preferred embodiments, the DNA sequence comprises the cDNA sequence of FIG. 1*b* from bp 36 to bp 1433, or the cDNA sequence of FIG. 1*b,* from bp 36 to bp 99, followed downstream by the sequence from bp 166 to bp 1433.

A method for producing a protein having biological activity for blood coagulation mediated by Factor VIIa through establishing a mammalian host cell that contains a DNA construct as described above is also disclosed. The mammalian host cell is subsequently grown in an appropriate medium, and the protein product encoded by the DNA construct is isolated. The protein product is then activated to generate Factor VIIa.

Other aspects of the invention will become evident upon reference to the following detailed description and attached drawings.

BRIEF DESCRIPTION OF THE DRAWINGS

FIG. 1a illustrates the partial Factor VII cDNA sequence produced by joining portions of cDNA clones λVII2115 and λVII1923.

FIG. 1b illustrates the Factor VII cDNA sequence of λVII2463. Arrows indicate the extent of the deletion in the sequence of λVII565. Numbers above the sequence designate amino acids. Numbers below designate nucleotides.

FIG. 2a illustrates the amino acid sequences of the amino terminal regions of several clotting factors.

FIG. 2b illustrates a comparison of the amino acid sequence of Factor VII obtained from protein sequencing with that encoded by the cDNA.

FIG. 3 illustrates the joining of Factor IX leader sequences to a sequence encoding a consensus calcium binding domain.

FIG. 7 illustrates the nucleotide sequence of a Factor IX/Factor VII cDNA fusion.

BEST MODE FOR CARRYING OUT THE INVENTION

Figure 4:
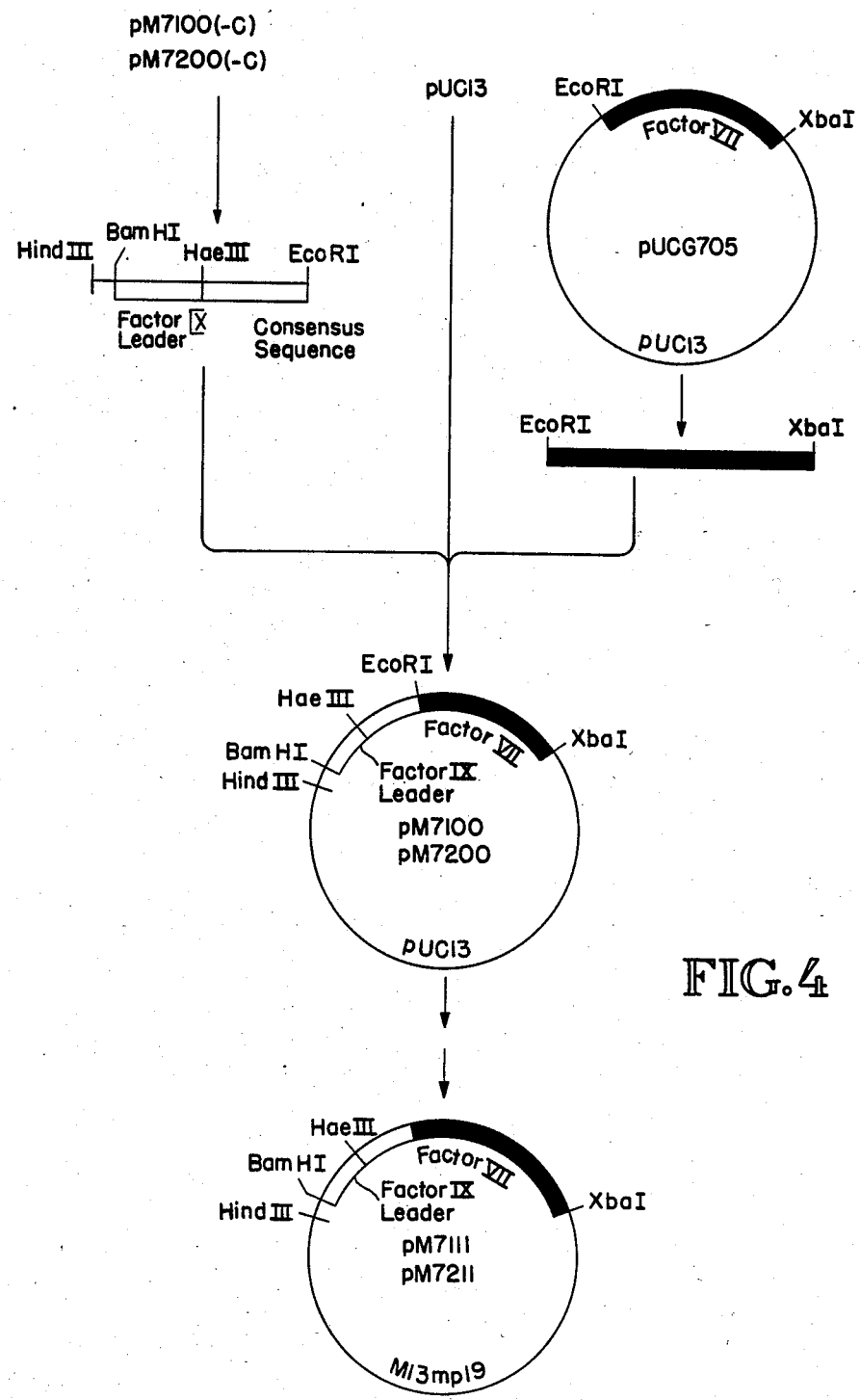
FIG. 4 illustrates the joining of the Factor IX-consensus sequence hybrids to a partial Factor VII cDNA to produce an in-frame coding sequence.

Prior to setting forth the invention, it may be helpful to an understanding thereof to set forth definitions of certain terms to be used hereinafter.

Complementary DNA or cDNA: A DNA molecule or sequence which has been enzymatically synthesized from the sequences present in a mRNA template.

DNA Construct: A DNA molecule, or a clone of such a molecule, either single- or double-stranded, which may be isolated in partial form from a naturally occurring gene or which has been modified to contain segments of DNA which are combined and juxtaposed in a manner which would not otherwise exist in nature.

Plasmid or Vector: A DNA construct containing genetic information which may provide for its replication when inserted into a host cell. A plasmid generally contains at least one gene sequence to be expressed in the host cell, as well as sequences which facilitate such gene expression, including promoters and transcription initiation sites. It may be a linear or closed circular molecule.

Joined: DNA sequences are said to be joined when the 5' and 3' ends of one sequence are attached, by phosphodiester bonds, to the 3' and 5' ends, respectively, of an adjacent sequence. Joining may be achieved by such methods as ligation of blunt or cohesive termini, by synthesis of joined sequences through cDNA cloning, or by removal of intervening sequences through a process of directed mutagenesis.

Leader Peptide: An amino acid sequence which occurs at the amino terminus of some proteins and is generally cleaved from the protein during subsequent processing and secretion. Leader peptides comprise sequences directing the protein into the secretion pathway of the cell. As used herein, the term "leader peptide" may also mean a portion of the naturally occurring leader peptide.

Domain: A three-dimensional, self-assembling array of specific amino acids in a protein molecule which contains all or part of the structural elements necessary for some bilogical activity of that protein.

Biological Activity: A function or set of functions performed by a molecule in a biological context (i.e., in an organism or an in vitro facsimile). Biological activities of proteins may be divided into catalytic and effector activities. Catalytic activities of clotting factors generally involve the activation of other factors through the specific cleavage of precursors. Effector activities include specific binding of the biologically active molecule to calcium or other small molecules, to macromolecules such as proteins, or to cells. Effector activity frequently augments, or is essential to, catalytic activity under physiological conditions. Catalytic and effector activities may, in some cases, reside within the same domain of a protein.

For Factor VIIa, biological activity is characterized by the mediation of blood coagulation through the extrinsic pathway. Factor VIIa activates Factor X to Factor Xa, which in turn converts prothrombin to thrombin, thereby initiating the formation of a fibrin clot. Because the activation of Factor X is common to both the extrinsic and intrinsic pathways of blood coagulation, Factor VIIa may be used to treat individuals severely deficient in the activities of Factor IX, Factor VIII or Von Willebrand Factor.

The biological activity of Factor IX is characterized by the mediation of blood coagulation through the intrinsic pathway. Factor IX is activated to Factor IXa by Factor XIa. Factor IXa then activates Factor X to Factor Xa in the presence of Factor VIIIa, phospholipid, and calcium ions. Factor Xa then acts in the conversion of prothrombin to thrombin, initiating the formation of a fibrin clot.

As noted above, the isolation of Factor VII from human plasma is a time-consuming and expensive process since the factor is a rare protein present only at a concentration of approximately 300 micrograms per liter of blood. In addition, it is difficult to separate from prothrombin, Factor IX and Factor X and is susceptible to proeteolytic attack during purification (Kisiel and McMullen, ibid). Although single-chain human Factor VII has been purified to homogeneity (Kisiel and Mc-Mullen, ibid), the published purification methods are generally limited by low yield and/or contamination by other coagulation factors.

Factors VII and IX are produced in the liver and require vitamin K for their biosynthesis. Vitamin K is necessary for the formation of specific gamma-carboxyglutamic acid residues in the factors. These unusual amino acid residues, which are formed by a post-translational modification, bind to calcium ions and are responsible for the interaction of the protein with phospholipid vesicles. In addition, Factors VII and IX each contain one $\beta$-hydroxyaspartic acid residue which is also formed after the proteins have been translated. However, the role of this amino acid residue is not known.

Given the fact that the activities of Factors VII and IX are dependent upon post-translational modifications involving the gamma carboxylation of specific glutamic acid residues, and may also be dependent upon the hydroxylation of a specific aspartic acid residue, it is unlikely that an active product could be produced through the cloning and expression of Factors VII and IX in a microorganism.

Accordingly, the present invention provides a method of producing a protein having biological activity for blood coagulation mediated by Factor VIIa using stably transfected mammalian cells. In addition, the present invention also provides a method of producing a protein having biological activity for blood coagulation mediated by Factor IX.

As noted above, Factors VII and IX require vitamin K for their biosynthesis. In addition, the plasma proteins prothrombin, Factor X, Protein C, and Protein S also require vitamin K for their biosynthesis. The amino-terminal portions of these proteins, which contain gamma-carboxyglutamic acid residues, are homologous in both amino acid sequence and in biological function (FIG. 2a). Further, the carboxy-terminal portions of Factor VII, prothrombin, Factor IX, Factor X, and Protein C determine their specific serine protease functions.

Factor VII is a trace plasma protein, and the mRNA encoding Factor VII is believed to be rare. Consequently, purification of Factor VII from plasma in sufficient quantities to permit extensive sequence analysis and characterization remains difficult. Degradation of Factor VII during purification, even in the presence of protease inhibitors, was noted by Kisiel and McMullen (ibid). Due to these difficulties, Factor VII has been poorly characterized, compared to other more abundant components of the blood coagulation system. Indeed, the work of Kisiel and MuMullen (ibid) yielded sequence information for only 10 residues of each chain of Factor VII, and in each sequence the identification of two residues was tentative. Partial amino acid sequence data for Bovine Factor VII have also been published (DiScipio et al., ibid).

The presumed rarity of Factor VII mRNA has contributed to the lack of knowledge of the Factor VII gene. The success of conventional cDNA cloning techniques is dependent on a sufficient quantity of mRNA for use as a template. Premature termination of reverse transcription results in the production of cDNA clones lacking the 5' end and this condition is exacerbated by low mRNA levels. Several strategies for cDNA cloning of low abundance message have been developed (Maniatis et al., *Molecular Cloning: A Laboratory Manual*, Cold Spring Harbor Laboratory, 1982), but a lack of knowledge of the amino acid sequence of the product of interest makes it impossible to predict the DNA sequence and to design appropriate oligonucleotide probes. While it may be relatively straightforward to obtain a partial cDNA clone of a gene encoding a rare protein by using these advanced strategies, full-length cDNA clones of genes encoding rare proteins such as Factor VII remain exceedingly difficult to obtain.

In comparison to Factor VII, Factor IX is a relatively abundant protein and the sequence of a cDNA clone of the human Factor IX gene is known (Kurachi and Davie, *Proc. Natl. Acad. Sci. USA* 79: 6461–6464, 1982; and Anson et al., EMBO J. 3: 1053–1060, 1984). The structure of the Factor IX gene has been characterized and the amino acid sequence of the protein has been determined on the basis of the known nucleotide sequence. Some protein sequence data have also been published for human and bovine Factor IX and the sequences analyzed (DiScipio et al., ibid). The amino terminal portion of the protein contains 12 glutamic acid residues that are converted to $\beta$-carboxyglutamic acid (Gla) residues in the mature protein. The cleavage sites involved in the activation of Factor IX have also been identified (Kurachi and Davie, ibid). A sequence at the 5' end of the Factor IX cDNA clone codes for a signal peptide which is typical of those found in most secreted proteins (Kurachi and Davie, ibid). The expression of the Factor IX gene through recombinant DNA methods has not been previously reported.

Because of the difficulty in obtaining a full-length cDNA clone of the Factor VII gene, three novel approaches were adopted to supply the 5' end of the coding sequence, including the region encoding the leader peptide. According to the first method, a partial cDNA clone for Factor VII is joined to a fragment encoding the leader peptide and 5' portion of Factor IX. This approach is based on the observation that the amino-terminal portions of the two molecules are responsible for the calcium binding activities of the respective proteins and the discovery that the calcium binding activity of Factor IX can substitute for that of Factor VII. The resultant polypeptide retains the biological activity of authentic Factor VII because the specific serine protease activities of the coagulation factors reside in the carboxy-terminal regions of the molecules. The second approach combines the partial cDNA clone with a DNA sequence encoding the leader and amino-terminal regions of Factor VII. The partial cDNA and amino acid sequences of Factor VII disclosed herein enable the screening of a genomic DNA library or cDNA library for clones comprising the 5' portion of the Factor VII gene. The third approach involves joining the partial cDNA clone to hybrid coding sequences comprising a cDNA fragment encoding the leader peptide of Factor IX and a synthetic gene segment encoding a consensus calcium binding domain or a predicted amino terminal sequence for Factor VII. The coding sequence for the amino terminus of Factor VII was established through previously unpublished amino acid sequence data disclosed herein. The consensus sequence was derived from the Factor VII data and published sequence data for other vitamin K-dependent plasma proteins.

Consistent with the approach described above for screening for clones comprising the 5' portion of the Factor VII gene, the inventors have been successful in obtaining a full-length, correct cDNA that is suitable for expression.

Among the cDNA clones that were generated, a clone designated "λVII2463" contained the largest Factor VII cDNA insert. It was found to contain the entire coding sequence for Factor VII. This clone included a 35 nucleotide 5' untranslated region, 180 nucleotides coding for a 60 amino acid leader, 1218 nucleotides coding for the 406 amino acid mature protein, a stop codon, 1026 nucleotides of 3' untranslated sequence, and a 20 base poly(A) tail (beginning at position 2463). This cDNA has now been sequenced in its entirety on both strands. A comparison of it with two cDNA inserts isolated earlier from clones λVII2115 and λVIII923, revealed that λVII2463 contains, on a single EcoRI fragment, a Factor VII cDNA coding for Factor VII leader and mature protein sequences.

A second clone, λVII565, was isolated that contained a cDNA insert that was identical to the cDNA of clone λVII2463 from nucleotide 9 to nucleotide 638, except that it lacked nucleotides 100 to 165 (FIG. 1b). In comparing the cDNAs to Factor VII genomic DNA, the absent sequences correspond precisely to one exon-like region. Therefore, two Factor VII cDNAs have been obtained which appear to reflect alternative mRNA splicing events.

The leader encoded by λVII2463 is exceptionally long (60 amino acids) and has a very different hydrophobicity profile when compared with Factor IX, protein C and prothrombin. This leader contains two mets, at positions $-60$ and $-26$. Initiation most likely begins at the first met, since a hydrophobic region, typical of signal peptides, follows the met at position $-60$, but not the met at $-26$. It is interesting that the absent sequence in λVII565, which corresponds precisely to an exon-like region in the genomic clone, results in a 38 amino acid leader with a hydrophobicity pattern more analogous to Factor IX, protein C, and prothrombin.

Since it was not clear then which, if either, of the leaders described above was authentic, an additional approach was initiated in an effort to analyze the 5' end sequence. Briefly, this approach included the construction and screening of a human genomic DNA library, and the identification of genomic clones comprising Factor VII gene sequences. The 5' portion of the genomic sequence was subsequently joined to the cDNA to construct a full-length clone.

In an additional construct, a 5' Factor VII cDNA fragment of λVII565 containing all of the leader and 29 amino acids of the mature coding sequence was ligated to a fragment of the cDNA of λVII2463 (containing the remainder of the mature protein and 3'-untranslated sequences). This "565-2463" sequence encodes a full-length Factor VII cDNA sequence as a single EcoRI fragment.

The DNA sequences described above are then inserted into a suitable expression vector which is in turn used to transfect a mammalian cell line. Expression vectors for use in carrying out the present invention will comprise a promoter capable of directing the transcription of a foreign gene in a transfected mammalian cell. Viral promoters are preferred due to their efficiency in directing transcription. A particularly preferred such promoter is the major late promoter from adenovirus 2. Such expression vectors will also contain a set of RNA splice sites located downstream from the promoter and upstream from the insertion site for a gene encoding a protein having biological activity for blood coagulation. Preferred RNA splice site sequences may be obtained from adenovirus and/or immunoglobulin genes. Also contained in the expression vectors is a polyadenylation signal, located downstream of the insertion site. Viral polyadenylation signals are preferred, such as the early or late polyadenylation signals from SV40 or the polyadenylation signal from the adenovirus 5: EIb region. In a particularly preferred embodiment, the expression vector also comprises a viral leader sequence, such as the adenovirus 2 tripartite leader, located between the promoter and the RNA splice sites. Preferred vectors may also include enhancer sequences, such as the SV40 enhancer.

Cloned DNA sequences may then be introduced into cultured mammalian cells by calcium phosphate mediated transfection. (Wigler et al., Cell 14: 725, 1978; Corsaro and Pearson, Somatic Cell Genetics 7: 603, 1981; Graham and Van der Eb, Virology 52: 456, 1973.) A precipitate is formed of the DNA and calcium phosphate and this precipitate is applied to the cells. A portion of the cells take up the DNA and maintain it inside the cell for several days. A small fraction of the cells (typically $10^{-4}$) stably integrate the DNA into the genome. In order to identify these stable integrants, a gene that confers a selectable phenotype (a selectable marker) is generally introduced along with the gene of interest. Preferred selectable markers include genes that confer resistance to drugs, such as G-418 and methotrexate. Selectable markers may be introduced into the cell on a separate plasmid at the same time as the gene of interest or they may be introduced on the same plasmid. A preferred selectable marker is the gene for resistance to the drug G-418, which is carried on the plasmid pKO-neo (Southern and Berg, J. Mol. Appl. Genet. 1: 327–341, 1982). It may also be advantageous to add additional DNA, known as "carrier DNA", to the mixture which is introduced into the cells. After the cells have taken up the DNA, they are allowed to grow for a period of time, typically 1–2 days, to begin expressing the gene of interest. Drug selection is then applied to select for the growth of cells which are expressing the selectable marker in a stable fashion. Clones of such cells may be screened for expression of the protein of interest.

Factor VII and Factor IX produced by the transfected cells may be removed from the cell culture media by adsorption to barium citrate. Spent medium is mixed with sodium citrate and barium chloride and the precipitate collected. The precipitated material may then be assayed for the presence of the appropriate clotting factor. Further purification may be achieved through immunoadsorption. It is preferred that the immunoadsorption column comprise a high-specificity monoclonal antibody. Alternatively, purification of the barium citrate precipitated material may be accomplished by more conventional biochemical methods or by high-performance liquid chromatography.

Conversion of single-chain Factor VII to active two-chain Factor VIIa may be achieved using Factor XIIa as described by Hedner and Kisiel (J. Clin. Invest. 71: 1836–1841, 1983), or with other proteases having trypsin-like specificity, such as Factor IXa, Kallikrein, Factor Xa, and thrombin, (Kisiel and Fujikawa, Behring Inst. Mitt. 73: 29–42, 1983).

In summary, the present invention provides a method for the production of proteins having the activity of vitamin K-dependent blood coagulation factors using transfected mammalian cells. Gene sequences encoding the specific serine protease domains of the coagulation factors are isolated from cDNA libraries. Sequences encoding the leader peptides and calcium binding domains are isolated from cDNA or genomic libraries or constructed from synthesized oligonucleotides. The sequences are then joined in an appropriate expression vector so as to encode a protein having the desired biological activity for blood coagulation. The resulting vector and a plasmid containing a drug resistance marker are co-transfected into appropriate mammalian tissue culture cells. Transfected cells may then be selected by addition of the appropriate drug, such as G-418. The protein products are then purified from the cell growth media and assayed for biological activity in a blood coagulation assay and for immunological cross-reactivity using antibodies prepared against authentic human clotting factors.

To summarize the examples which follow, Example 1 discloses the cloning of a full-length cDNA sequence for Factor VII. Example 2 discloses a partial amino acid sequence of human Factor VII, including the sequence of approximately 30 amino acids at the amino terminus. Example 3 discloses the construction and screening of a human genomic DNA library and the identification of genomic clones comprising Factor VII gene sequences. Example 4 discloses the construction of two hybrid gene segments, each comprising a cDNA fragment encoding the leader peptide of Factor IX and a synthesized double-stranded fragment encoding a consensus calcium binding domain. The hybrid sequences are then joined to partial cDNA clones of Factor VII. Using in vitro mutagenesis, the consensus sequence was the altered to conform to the protein sequence data for Factor VII. Example 5 describes the construction of a gene sequence encoding a fusion protein comprising the calcium binding domain of Factor IX and the specific serine protease domain of Factor VII. Example 6 describes the construction of the vector pD2 for use in expressing proteins having biological activity for blood coagulation in transfected mammalian cells. The gene fusion described in Example 5 is expressed using this vector. Example 7 describes the use of the vector pD2 to express a gene for Factor IX in a transfected mammalian cell line. Example 8 describes the construction of the vector pM7135, which contains DNA sequences encoding a primary translation product comprising the leader sequence of Factor IX fused to Factor VII. This vector may be used to produce a protein having the activity of Factor VII in a transfected mammalian cell line. Example 9 describes the expression of Factor VII using cDNA sequences, and the expression of Factor VII from a genomic-cDNA hybrid sequence.

The following examples are offered by way of illustration and not by way of limitation.

EXAMPLES

Restriction enzymes were obtained from Bethesda Research Laboratories (BRL) and New England Biolabs and were used as directed by the manufacturer, unless otherwise noted. Oligonucleotides were synthesized on an Applied Biosystems Model 380 A DNA synthesizer and purified by polyacrylamide gel electrophoresis on denaturing gels. E. coli cells were transformed as described by Maniatis et al. (*Molecular Cloning: A Laboratory Manual,* Cold Spring Harbor Laboratory, 1982). M13 and pUC cloning vectors and host strains were obtained from BRL. Factor VII was prepared from human plasma as described by Kisiel and McMullen (ibid).

EXAMPLE 1

Cloning of a Partial Factor VII cDNA

A. Construction of a human liver cDNA library.

A cDNA library was prepared from human liver mRNA by the method of Chandra et al., *Proc. Natl. Acad. Sci.* U.S.A. 80: 1845–1848, 1983. The cDNA preparation was sedimented through an alkaline sucrose gradient (Monahan et al., *Biochemistry* 15: 223–233, 1976) and fractions containing species of greater than about 1000 nucleotides were pooled. The first strand preparation was made double-stranded using reverse transcriptase (Chandra et al., 1983), treated with S1 nuclease, and the residual staggered ends filled-in using DNA Polymerase I (Klenow fragment) in the presence of all four deoxyribonucleotide triphosphates (Maniatis et al., *Molecular Cloning: A Laboratory Manual,* Cold Spring Harbor Laboratory, 1982). The blunt-ended cDNA was treated with Eco RI methylase and ligated to phosphorylated Eco RI linkers using $T_4$ DNA ligase (Maniatis et al., ibid). The ligated DNA preparation was exhaustively digested with Eco RI to remove excess linker sequences and double-stranded DNAs greater than about 1000 base pairs in length were purified by neutral sucrose gradient centrifugation (Maniatis et al., ibid). Native λgt11 DNA was ligated into concatemers, digested to completion with Eco RI, and the 5′ terminal phosphates were removed by treatment with bacterial alkaline phsophatase. The pooled human liver cDNA was ligated with the phage DNA, packaged in vitro (Maniatis et al., ibid), and used to infect *E. coli* Y1088 (Young and Davis, Science, 222: 778–782, 1983). Approximately $14 \times 10^6$ primary phage plaques were generated in this library, composed of seven libraries of $-2 \times 10^6$ plaques each. Greater than 90% of these were recombinants containing human DNA inserts, based on their lack of β-galactosidase activity and characterization of 20 random clones by Eco RI digestion followed by agarose gel electrophoresis. The cDNA library, in the form of phage particles, was purified by cesium chloride gradient centrifugation and stored in SM buffer (Maniatis et al., ibid).

B. Screening of the human liver cDNA library for Factor VII clones.

The human liver expression cDNA library described above was screened for specific antigen (Young and Davis, ibid) using an $^{125}$I-labelled monoclonal Factor VII antibody prepared by the method of Brown et al. (*J. Biol. Chem.* 225: 4980–4983, 1980) using purified Factor VII. Screening of $6 \times 10^6$ phage plaques identified one isolate, designated λVII2115, which gave a positive response with the antibody.

The phage clone λVII2115 was tested against two other anti-Factor VII monoclonal antibodies and a rabbit polyclonal antibody to Factor VII. Isolate λVII2115 gave a positive response to all these anti-Factor VII antibodies.

DNA was prepared from a plate lysate (Maniatis et al., pp. 65–66, 1982) of λVII2115. Digestion of this DNA with Eco RI liberated an insert of 2139 base pairs. This insert was subcloned into M13 phage vectors (Messing, *Meth. in Enzymology* 101: 20–77, 1983; and Norrander et al., Gene 26: 101–106, 1983) for chain termination dideoxy DNA sequencing (Sanger et al., *Proc. Natl. Acad. Sci. U.S.A.* 74: 5463–5476, 1977). This cDNA insert contains Pst I sites at positions 214, 839, and 1205 (designated Pst Ia, Pst Ib, and Pst Ic, respectively, in FIG. 1a) and a Sma I site located at position 611. The following M13 templates were sequenced:
(1) full-length (2139 bases) Eco RIa→Eco RIb fragment in M13mp18 (designated clone F7-1);
(2) Pst Ia→Eco RIa 214 base fragment in M13mp19 (F7-2);
(3) Pst Ia→Pst Ib 625 base fragment in M13mp18 (F7-3);
(4) Pst Ib→Pst Ia 625 base fragment in M13mp18 (F7—7);
(5) Sma I→Pst Ib 228 base fragment in M13mp10 (F7-8);
(6) Pst Ib→Pst Ic 366 base fragment in M13mp18 (F7-9);
(7) Pst Ic→Pst Ib 366 base fragment in M13mp18 (F7-10);
(8) Pst Ic→Eco RIb 930 base fragment in M13mp19 (F7-11); and
(9) Eco RIb→Eco RIa full-length fragment in M13mp18 (F7-12)
(restriction site designations refer to FIG. 1a).

The data confirmed the sequence on both strands for 91% of the coding region and 15% of the 3' non-coding region and yielded single-stranded sequence information for the remaining 9% of the coding region and 85% of the non-coding region.

Comparison of the amino acid sequence predicted from the cDNA sequence with the known amino acid sequence data of Kisiel and McMullen (*Thrombosis Research* 22: 375, 1981) and the amino acid sequence shown below (Example 2) revealed an anomaly which could be explained by the absence of three nucleotides in the DNA sequence near position 400. To obtain additional sequence data, λVII2115 was digested with Eco RI, and the Factor VII coding fragment was inserted into pUC 13 (Vieira and Messing, Gene 19: 259-268, 1982; and Messing, ibid) which had been digested with Eco RI. The resultant recombinant plasmid, designated pUCVII2115, was digested with Xba I which cut at position 328. The digested sample was divided in half: half was labeled with $\alpha^{32}P$ dCTP and DNA Polymerase I (Klenow fragment) (Englund, P. T., J. Mol. Bio. 66: 209, 1972); the other half was labeled with $\gamma^{32}P$ ATP and polynucleotide kinase (Chaconas et al., *Biochem. Biophys. Res. Comm.* 66: 962, 1975). The labeled plasmids were then recut with Pst I to yield 113 and 509 base pair fragments. Both strands of each of these were sequenced by the method of Maxam and Gilbert (*Meth. in Enzymology* 74: 560, 1980). The 113 base pair fragment was sequenced in its entirety and 210 base pairs of the 509 base pair fragment were sequenced. These sequences revealed three additional bases (one C and two G's) which rendered the DNA sequence data in agreement with the protein sequence data, indicating that the previous anomalous results arose from compressions on the sequencing gel due to secondary structure involving G's and C's. The sequence of the last 9% of the coding region on both strands was also confirmed.

Further analysis of the sequence of the pUCVII2115 insert confirmed that a portion of this cloned fragment encoded a sequence of 11 amino acids known to be at the cleavage site of Factor VII (Kisiel and McMullen, *Thrombosis Research* 22: 375, 1981). Comparison of this sequence to Factor IX (Davie et al., ibid) and Factor X (Leytus et al., Proc. Natl. Acad. Sci. U.S.A. 81: 3699-3702, 1984) amino acid sequences suggested that the clone contained the sequence for Factor VII beginning at (approximately) nucleotides coding for amino acid 36 of the mature Factor VII protein and continuing through approximately 1000 coding and 1100 noncoding nucleotides and poly A sequence. In addition, it was found that this clone had frameshift mutations in the 3' coding portion.

In order to obtain the correct 3' coding region, all 14 million clones of the seven λgt11 cDNA libraries were screened by plaque hybridization (Benton and David, Science 196: 180-181, 1977) with nick-translated cDNA of λVII2115 (Maniatis et al., pp. 109-112, 1982).

Seven positive isolates were then screened by dideoxy sequencing of pUC plasmids into which the cDNA inserts had been subcloned (Wallace et al., Gene 16: 21, 1981). The λgt11 clones were digested with Eco RI and the Factor VII fragments were inserted into pUC13 which had been cleaved with Eco RI. All except one of these were found to start at a position corresponding to base 212 of the insert in λVII2115; the one exception consisted only of 3' non-coding sequence. One of the clones starting at base 212 was selected for analysis and was designated clone pUCVII1923.

Because analysis of pUCVII2115 indicated the presence of frameshift mutations between positions 657 and 815, pUCVII1923 was first analyzed in this region by Maxam-Gilbert sequencing. Plasmid pUCVII1923 was digested with Nar I (position 779 in FIG. 1a). The cut DNA was labeled with $\alpha^{32}P$ dCTP using DNA Polymerase I (Klenow fragment) and subsequently digested with Ava I (which cleaves at the same site as Sma I in FIG. I) and Taq I (site at 1059), yielding a Nar I-Ava I 166 bp fragment and a 200 bp Nar I-Taq I fragment. Each of these was sequenced. A C, missing in pUCVII2115, was found at position 697 and another C, also missing in pUCVII2115, was found at position 798.

The rest of the sequence of the coding region of pUCVII1923 was shown to be correct by sequencing by the dideoxy method on an M13 subclone of the entire insert of pUCVII1923. The Lac primer ZC87 (Table 1) was used to sequence from position 212 (FIG. 1a) to 512; primer ZC218 (CTCTGCCTGCCGAAC) was used to sequence from 715 to 1140 and primer ZC217 (ATGAGAAGCGCACGAAG) was used for sequencing from 720 to 350. Since the pUCVII2115 insert is correct from position 13 (positions 1-12 include an artificial linker) to 695, and pUCVII1923 is correct from position 212 to the end, the two were spliced together to yield a molecule correct from position 13 (FIG. 1a) to the end. A convenient point utilized for this splice is the Xba I site at position 328. The sequence of the spliced corrected molecule is shown in FIG. 1a.

Because a full-length Factor VII clone was difficult to obtain by cDNA cloning, three strategies were adopted to provide the missing coding sequence and the necessary upstream processing and signal sequences. The first strategy was to obtain the needed sequence from a human genomic DNA library or through additional screening of cDNA libraries. The second approach was to synthesize the necessary 5' coding sequence, based on the amino acid sequence data for Factor VII (Example 2) and the published sequences of the genes encoding vitamin K-dependent clotting factors (Kurachi and Davie, ibid; and Davie et al., ibid), and join this to a portion of the prepro sequence of Factor IX. The third strategy relies on the functional homology of the amino terminal regions of Factor VII and Factor IX. A sequence was constructed which comprised the coding regions for the leader and amino-terminal portion of Factor IX. This was then fused in the proper orientation to the partial Factor VII cDNA.

In order to obtain DNA sequences that comprise the entire DNA sequence of Factor VII, an attempt was made to isolate the remaining 5' DNA sequence. This was accomplished through the utilization of the 5' terminal 0.3 kb EcoRI-XbaI fragment from the cDNA insert of λVII2115 to screen a cDNA library comprising $2 \times 10^6$ phage. The library was constructed using poly(A) mRNA from HepG2 cells following an adaptation of the method of Gubler and Hoffman (Gene 25: 263-269, 1983). The RNA was reverse transcribed to generate first strand cDNA, followed by second strand synthesis using DNA polymerase I and RNase H. Following EcoRI methylation and passage over a Sepharose 6B column, the DNA terminal were blunted with $T_4$ DNA polymerase. EcoRI linkers were added and excess linkers were removed by digestion with EcoRI and chromatography on Sepharose CL 2B. The DNA in the void volume was collected and ligated to λgt11 which had been digested with EcoRI and treated with calf intestinal phosphatase. The DNA was packaged and infected into E. coli Y1088. Several positives were detected, and the EcoRI fragments were subsequently subcloned into M13 phage vectors for dideoxy sequencing using either the M13 universal primer or Factor VII specific oligonucleotides.

From these, three new cDNA clones of Factor VII were obtained, and their sequences completely determined. The largest of these cDNAs, from a clone designated λVII2463, was found to contain the entire coding sequence for Factor VII. This clone included a 35 nucleotide 5' untranslated region, 180 nucleotides coding for a 60 amino acid leader, 1218 nucleotides coding for the 406 amino acid mature protein, a stop codon, 1026 nucleotides of 3' untranslated sequence, and a 20 base poly(A) tail (beginning at position 2463). This cDNA has now been sequenced in its entirety on both strands. A comparison of it with two cDNAs isolated earlier from clones λVII2115 and λVII1923 revealed that clone λVII2463 contains an additional 321 nucleotides upstream of the insert in λVII2115 and 519 nucleotides upstream of the insert in λVII1923. The overlapping Factor VII sequences of λVII2463 and these two previous cDNAs agree, except that the cDNA of λVII2463 does not contain single base deletions at positions 1005 and 1106, which were detected in the cDNA of λVII2115. Thus, λVII2463 contains, on a single EcoRI fragment, a Factor VII cDNA coding for Factor VII leader and mature protein sequences.

An additional cDNA, λVII565, was isolated and found to contain 5' terminal Factor VII sequences, but was truncated within the coding sequences. Its 5' end maps at nucleotide 9 (FIG. 1b).

When compared with full-length λVII2463, λVII565 was found to lack a sequence corresponding to one exon-like region within the leader sequence. Bases 100-165 are absent from λVII565 (FIG. 1b). The absent sequences correspond precisely to one exon-like region by comparison with genomic sequence data (as described in Example III). Thus, the λVII565 structure may be a consequence of alternative splicing events in the leader sequence.

The leader encoded by λVII2463 is exceptionally long (60 amino acids) and has a very different hydrophobicity profile when compared with Factor IX, protein C and prothrombin. This leader contains two Mets, at positions $-60$ and $-26$. Initiation most likely begins at the first Met, since a hydrophobic region, typical of signal peptides, follows the Met at position $-60$, but not the Met at $-26$. It is interesting that the absent sequences in λVII565, which corresponds precisely to an exon-like region in the genomic clone, results in a 38 amino acid leader with a hydrophobicity pattern more analogous to the above proteins.

EXAMPLE 2

Amino Acid Sequence of Human Factor VII

The elucidation of the amino acid sequence of human Factor VII was desired in order to confirm the identity of putative cDNA clones, substantiate the sequence of factor VII cDNA, provide information allowing for the synthesis of specific oligonucleotide probes to screen cDNA and genomic libraries for clones containing the 5' sequence, and to construct a synthetic fragment encoding the amino-terminal portion of Factor VII. Although limited amino acid sequence was provided by Kisiel and McMullen (ibid), more information was needed.

Purified human Factor VIIa (Kisiel and McMullen, ibid) was reduced and carboxymethylated by the method of Crestfield et al., J. Biol. Chem. 238: 622, 1963. The light and heavy polypeptide chains of carboxymethylated Factor VIIa were separated by high-performance liquid chromatography (HPLC) on a Micro Pak C18 reverse phase column (Varian Corp.) by generating a gradient of 0.1% TFA in distilled water (A) and 0.1% TFA in acetonitrile (B) from 0-40% B in 5 minutes, 40-80% B in 25 minutes and 80-100% B in 5 minutes. Approximately 300 picomoles of each peptide chain were analyzed by automated Edman degradation using a Gas-Phase Protein Sequencer (Applied Biosystems, Inc.). Eighteen and 29 residues were identified at the amino-termini of the heavy and light polypeptide chains, respectively. The amino-terminal sequence of the heavy chain of Factor VIIa was consistent with that encoded by cDNA clone pUCVII2115 (FIG. 2b). Amino acid residues are designated within FIGS. 2a and 2b by single letter code as follows: A, alanine; C, cysteine; D, aspartic acid; E, glutamic acid; F, phenylalanine; G, glycine, H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine; X indicates an unknown residue and * indicates that the Gla residues (γ) were assigned by homology to the structures of other known clotting factors and by the absence of any other phenylthiohydantoin-amino acid at those positions. The gaps (—) are placed to provide the best alignment among the sequences. In addition, the information indicated that the amino acids at positions five and nine were lysines and not threonine and arginine, respectively, as previously reported (Kisiel and McMullen, ibid). The sequence analyses of the light chain of Factor VIIa, which originates from the amino-terminal region of Factor VII, fell short by approximately 6 residues to overlap with the structure encoded by the 5' end of cDNA clone pUCVII2115.

To obtain additional sequence data, two nanomoles of the carboxymethylated light chain were digested for 12 hours by bovine chymotrypsin (1:100 w/w, enzyme: substrate) in 0.1M ammonium bicarbonate, pH 7.8, at 37° C. The generated fragments were purified by HPLC on a Micro Pak C18 reverse phase column using the above solvents in a gradient of 0–38% B in 5 minutes, 30–60% B in 25 minutes and 60–80% B in 10 minutes. Peptides were identified by their U.V. absorption at 220 and 280 nm. Lyophilized peptides (approximately 1 nanomole each) were analyzed by Edman degradation. The results (FIG. 2b) confirmed much of the cDNA sequence in the corresponding region of clone pUCVII2115. In total, 113 of 152 residues (75%) of the light peptide chain of Factor VIIa were identified. This sequence is identical to that encoded by the known cDNA structure. Indirect evidence indicates Asn 145 is a site of carbohydrate attachment.

EXAMPLE 3

Cloning of the genomic Factor VII sequence

As one approach to providing the 5' end sequence lacking from the cDNA, a lambda phage library containing human fetal liver DNA (Law et al., Cell 15: 1157–1174) was screened with nick translated Factor VII cDNA. A portion of the genomic library was plated on E. coli LE392 (ATCC 33572) to produce a total of 7.2×10⁶ plaques (Maniatis et al., ibid, pp. 320–321). The phage plaques were adsorbed from the plates onto nictrocellulose and hybridized with the $^{32}$p-labeled cDNA according to the procedure of Benton and Davis (Science 196: 180, 1977). Eight clones were obtained and plaque purified.

Using a DNA fragment (Eco RIa-Xba I, FIG. 1) from the 5' end of the Factor VII cDNA (λVII2115) and standard techniques (Maniatis et al., ibid) those genomic clones containing 5' end sequences were identified. These phage were designated 7m1, 7m2 and 7m3. DNA was prepared from these recombinant phage and preliminary restriction endonuclease maps derived. Phage 7m1, which gave the strongest hybridization signal, was used to generate a more extensive restriction map and to place the Eco RI-Xba I cDNA sequences on this map by Southern blotting (Southern, J. Mol. Biol. 98: 503, 1975).

In order to determine if phage 7 ml contained the DNA sequences encoding the amino terminal amino acids of the Factor VII protein, Southern blots of phage DNA restriction digests were hybridized with mixtures of oligonucleotides whose sequences were deduced from the Factor VII amino terminal amino acid sequence. Oligonucleotides ZC188, ZC360, and ZC401 (Table 1) were radioactively labeled with T₄ polynucleotide kinase and hybridized to the phage DNA blots at a few degrees centigrade below their Tm (Wallace, R. B., et al., Nuc. Acids. Res. 6: 3543–3557, 1979). The results of this analysis indicated that a 3.7 kb Sst I fragment of 7m1 contained sequences hybridizing to these oligonucleotides. This Sst I fragment was subcloned into M13 for DNA sequence analysis. Results obtained using ZC360 as sequencing primer identified a region approximately 60 nucleotides in length, which corresponded to the amino-terminal protein sequence data.

TABLE 1

| Oligonucleotide | Sequence |
|---|---|
| ZC87 | TCC CAG TCA CGA CGT |
| ZC188 | GCC GGG CTCA CTC CTC CA GAA GGC GTTGG (with T/C, G/A, A/G variants) |
| ZC212 | GAC CTG CAG GAT CCA TGC AGC GCG TGA ACA TGA TCA TGG |
| ZC213 | GAG GCC TGG TGA TTC TGC CAT GAT CAT GTT CAC GCG CTG |
| ZC217 | ATG AGA AGC GCA CGA AG |
| ZC218 | CTC TGC CTG CCG AAC |
| ZC235 | GAT CCA TGC AGC GC |
| ZC249 | AGA ACA GCT TTG TTC TTT CA |
| ZC275 | GCC CCC ATT CTG GCA |
| ZC286 | CCA AAG AGG GCC AAC GCC TTC CTG GAG GAG AGA CCT GGG AGC CTG GAG AGA GAG TGT ATT GAG G |
| ZC287 | AAT ACA CTC TCT CTC CAG GCT CCC AGG TCT CTC CTC CAG GAA GGC GTT GGC CCT CTT TGG |
| ZC288 | AGC AGT GTA GCT TCG AGG AGA ACA GAG AGG TTT TCG AGG CCA GCG ACG |
| ZC289 | AAT TCG TCG CTG GCC TCG AAA ACC TCT CTG TTC TCC TCG AAG CTA CAC TGC TCC |
| ZC333 | CAG CTT CGT CCT GTC GCT GGC CTC |
| ZC336 | CCT CTT TGG GCC TGG TGA |
| ZC360 | CA TC TC TC TT CA (with C/T, C/T, C/T, C/T, G/A variants) |
| ZC401 | CGT AGC GTT CAG GCC CTC GAA GAT CTC GCG GGC CTC CTC GAA GCT ACA C |

Since genomic clone 7m1 was known to contain 7kb of sequences upstream of exon 2, this clone was anticipated to encode Factor VII 5'-untranslated sequences and the leader sequences up to the amino acid position −17. In order to confirm that exon 1 was encoded within genomic clone 7m1, the leader sequence information from clones λVII2463 and λVII565 was used to design oligonucleotides ZC528 and ZC529 (shown below).

AC528
5'                                                3'
TCA ACA GGC AGG GGC AGC ACT GCA GAG ATT

ZC529

-continued

```
5'                                              3'
TTC CAC GGC ATG TCC CGT GTT TCT CCT CCT
```

These were used to probe 7m1 DNA, and a subclone, 7SD, was found that hybridized to both oligonucleotides. Exon 1 was determined to be composed of two exonic sequences: exon 1a, which hybridized to ZC528 (corresponding to nucleotides 1 to 30 in λVII2463), and exon 1b, which hybridized to ZC528 (corresponding to nucleotides 119 to 148 in λVII2463). The intron sequences flanking both exons 1a and 1b have been sequenced: 1a contains a consensus splice donor sequence at the 3' end of the exon, and 1b is flanked on each terminus with a consensus splice acceptor (upstream of 1b) or donor (downstream of 1b) sequence. The position of exon 1a within genomic clone 7m1 has been precisely mapped, while that of exon 1b has been mapped within a defined region. Exon 1b sequences are present in λVII2463, while λVII565 appears to be derived from RNA spliced between exon 1a and exon 2, looping out the 1b exonic sequence.

A variety of 7m1 subclones in pUC and M13 vectors were prepared to facilitate sequencing the remaining exons. Appropriate oligonucleotides designed from the cDNA sequences, which correspond to exons 1 through 7, were used to sequence all but the last exon. The genomic sequence corresponds exactly to the cDNA sequences through these regions. In addition, the intron/exon boundaries for exons 1-7 have been determined, and most are now precisely mapped within clone 7m1. The intron sizes and position within the Factor VII gene are listed in Table 2.

TABLE 2

| Intron/Exon Junctions in the Factor VII Gene | | |
|---|---|---|
| Intron | Amino Acid Position | Intron Size (Kb) |
| A | −39 | >0.2 |
| B | −17 | >1.0 |
| C | 37/38 | 1.92 |
| D | 46 | 0.068 |
| E | 84 | ~2 |
| F | 131 | ~1 |
| G | 167/168 | 0.56 |
| H | 209 | 1.31 |

Phage 7m1 was known to lack the Factor VII 3'-terminus, which includes exon 8. In order to obtain these sequences, a 12-13 Rb-enriched Bam HI library in λL47.1 (Loenen and Brammer, Gene 10: 249, 1980; Maniatis, et al., ibid.), derived from human dermal primary fibroblast cells, was probed with two nick-translated Factor VII cDNA PstI fragments (corresponding to sequences in exon 7, and to 3'-untranslated sequences). A clone, designated 7DC1, was detected by both probes. Subsequent restriction endonuclease and Southern blot analysis established that clone 7DC1 overlaps with, and extends approximately 3 Kb beyond the terminus of, clone 7m1, and that it contains exon 8. The 3.9 Kb (XbaI-BamHI) fragment from 7DC1 DNA containing exon 8 was subcloned into M13, and sequence analysis was performed using oligonucleotides complementary to its 5' and 3' termini. The entire exon sequence is present in this clone.

EXAMPLE 4

Factor IX-Factor VII Hybrid Genes Containing a Synthesized Coding Sequence

A. Construction of a hybrid Factor IX leader-synthetic Factor VII 5' coding sequence.

The second alternative for obtaining the 5' coding sequence for Factor VII was synthesis of an appropriate double-stranded fragment, using a nucleotide sequence predicted on the basis of the amino terminal amino acid sequence of Factor VII, the amino acid sequences of other vitamin K-dependent clotting factors, and the known nucleotide sequence of other vitamin K-dependent clotting factor genes (Kurachi and Davie, ibid; Anson et al., EMBO J. 3: 1053–1060, 1984; and Davie et al., ibid). In order to provide the necessary secretion and processing signals for secretion of a mature Factor VII analog, this synthetic fragment (the consensus sequence) was joined to one of two leader sequences derived from a Factor IX cDNA clone. This strategy is outlined in FIG. 3.

A cDNA coding for human Factor IX was obtained from a library made with mRNA from human liver (Kurachi and Davie, ibid)., The Factor IX sequence was isolated from the pBR322 vector by digestion with Pst I and was inserted into the Pst I site of pUC13. This plasmid was designated FIX-pUC13. In order to remove the G-rich region which was present at the 5' end of the Factor IX insert as a result of cDNA cloning, a synthetic oligonucleotide adaptor was substituted for the 5' end of the cloned fragment. Oligonucleotides ZC212 and ZC213 (Table 1) were synthesized and annealed to generate a 22 base pair overlap, the fragment ends filled in and cut with appropriate restriction endonucleases, and the resulting fragment was joined to the Factor IX sequence.

To construct the adaptor, 100 pmoles each of ZC212 and ZC213 were lyophilized and resuspended in 10 ul of 10x kinase/ligase buffer (600 mM Tris pH 8.0, 100 mM $MgCl_2$, 100 nM DTT) plus 86 ul $H_2O$. The annealing reaction was run at 65° C. for 10 minutes, the mixture was slowly cooled to room temperature and put on ice. To this mixture was added 4 ul of 2.5 mM dNTP mix and 1 ul (8 units) $T_4$ DNA polymerase. The reaction was allowed to proceed 45 minutes at 14° C. Ten ul of 5M $NH_4OAc$ was then added and the DNA was extracted once with phenol/$CHCl_3$, twice with $CHCl_3$, and was precipitated with ethanol. The DNA was centrifuged and resuspended in 100 ul medium salt buffer (Maniatis et al., ibid, p. 100), digested with 9 units Pst I and 8 units Cfo I, and extracted as above.

The modified Factor IX sequence was then constructed by combining 0.16 pmoles of the synthetic Pst I-Cfo I adaptor fragment, 0.14 pmoles of a 1.4 kb Cfo I-Bam HI Factor IX fragment from FIX-pUC13, and 0.14 pmoles of a 2.7 kb Bam HI-Pst I pUC13 vector fragment in a 20 ul reaction containing 60 mM Tris-HCl pH 7.5, 10 mM $MgCl_2$, 10 mM DTT, and 0.9 units $T_4$ ligase. The reaction was incubated for 3 h at room temperature and used to transform competent E. coli JM83 (Messing, Recombinant DNA Technical Bulletin, NIH Publication No. 79-99, 2, No. 2, 43–48, 1979). The cells were plated with 50 ul of 2% X-gal (5 bromo-4-chloro-3 indolyl-β-D-galactoside) on L-broth containing 40 ug/ml ampicillin and incubated at 37° C. overnight. White colonies were picked onto another plate containing ampicillin and grown at 37° C. overnight. The colonies were blotted on Whatman 540 paper and the paper prepared for hybridization according to the method of Wallace et al. (Gene 16: 21, 1981), except the overnight incubation on chloramphenicol plates was omitted. The papers were incubated at 44° C. for 2 h in 0.9M NaCl, 0.09M Tris-HCl pH 7.5, 6 mM EDTA, 0.5% Nonidet P-40, 150 ug/ml $E.$ $coli$ tRNA. The papers were probed with $^{32}$p-labeled ZC235 (Table 1), a 14-mer that is specific for the altered 5' and sequence. Hybridization with $1-2\times10^6$ cpm per filter was carried out at 44° C. in the prehybridization buffer overnight. The filters were then washed 3 times in $6\times$SSC, 0.1% SDS at 4° C. and 3 times in $2\times$SSC, 0.1% SDS at 44° C. and exposed to X-ray film. Two positive clones were obtained. One of these clones was designated FIX (−G)→pUC13.

In order to confirm the sequence of the altered region of the Factor IX portion of the FIX(−G)→pUC13 construct, dideoxy sequencing directly on the pUC plasmid using the BRL reverse primer was performed using the method of Wallace et al., 1981 (ibid) using a primer end labeled with polynucloetide kinase and $\gamma^{32}$p ATP by the method of Chaconas et al. (ibid). The sequence was as predicted.

The resulting recombinant plasmid contains three Hae III cleavage sites, the first at position 39 in the Factor IX sequence (numbering is based on the published sequence of Anson et al. (ibid), beginning at the first ATG), the second at position 130, and a third in the pUC13 polylinker. The site at 130 is a single base pair upstream from the codons for the Lys-Arg processing site of the prepro Factor IX molecule. In the final Factor IX-Factor VII hybrid constructs, the Factor IX leader sequence, terminated at position 39 to 130, was joined to a synthetic double-stranded fragment comprising the predicted consensus sequence and the last 3 codons of the Factor IX leader sequence.

The synthetic consensus fragment was produced by joining oligonucleotides ZC286-ZC289 (Table 1) to form a double-stranded fragment. One hundred pmole of each oligonucleotide was lyophilized and resuspended in 20 ul of 1x kinase buffer and incubated overnight at 4° C.; then heated at 65° C. for 10 minutes. Two pools were made using the kinased oligonucleotides. Pool 1 contained ZC286+ZC287; pool 2 contained ZC288+ZC289. The pooled pairs were annealed 10 minutes at 65° C., then cooled to room temperature over a period of 2 hours and placed on ice for 30 minutes.

The modified Factor IX fragment was removed from FIX(−G)→pUC13 as a Hind III-Eco RI fragment. Approximately 20 ug of plasmid was digested with 30 units each of Hind III and Eco RI in 100 ul Hind III buffer (BRL) containing 4 ug RNase A at 37° C. overnight. The reaction was terminated by heating at 65° C. for 10 minutes, and the vector and Factor IX fragments were electrophoresed on a 1% agarose gel and purified by electro-elution. The Factor IX fragment was precipitated with ethanol, resuspended in buffer containing 400 ng/ul RNase A, and digested with 9 units of Hae III overnight at 37° C. The Hind III-Hae III 39 base pair Factor IX fragment was isolated from this digest by electrophoresis on a 1.5% agarose gel followed by electroelution. To obtain the Hind II-Hae III 130 base pair Factor IX fragment, FIX-pUC13 was digested with Eco RI and Hind III and the Factor IX fragment isolated as above. Approximately 3 ug of this Hind III-Eco RI fragment was digested with 6 units of Hae III at 37° C. and aliquots were removed at five minute intervals over 30 minutes into a solution containing 50 mm EDTA. The aliquots were pooled and the Hind III-Hae III 130 base pair fragment was purified by electrophoresis on a 5% acrylamide gel followed by electro-elution.

The final Factor IX-consensus sequence hybrids were prepared by joining, in a four-part ligation, oligonucleotide pools 1 and 2, Factor IX Hind III-Hae III (39 or 130 base pairs), and pUC13 Hind III-Eco RI. The resulting plasmids were used to transform $E.$ $coli$ HB101 (ATCC 33694). Colonies were screened by digestion of DNA with Eco RI and Hind III. The sequence comprising the 39 base pair Factor IX sequence joined to the synthetic consensus sequence is hereinafter referred to as mini-FIX-FVII. The plasmid containing this construct was designated pM7200(−C). The sequence comprising the 130 base pair Factor IX sequence joined to the synthetic consensus sequence is referred to as maxi-FIX-FVII. The plasmid containing this construct was designated pM7100(-C). The consensus sequence encodes a polypeptide comprising the amino acid sequence Ala-Asn-Ala-Phe-Leu-Gla-Gla-Arg-Pro-Gly-Ser-Leu-Gla-Arg-Gla-Cys-Lys-Gla-Gln-Cys-Ser-Phe-Gla-Gla-Ala-Arg-Gla-Ile-Phe-Gla-Gly-Leu-Asn-Arg-Thr-Lys-Leu.

B. Joining Factor IX-consensus sequence hybrid fragment to Factor VII cDNA clone.

Figure 5:
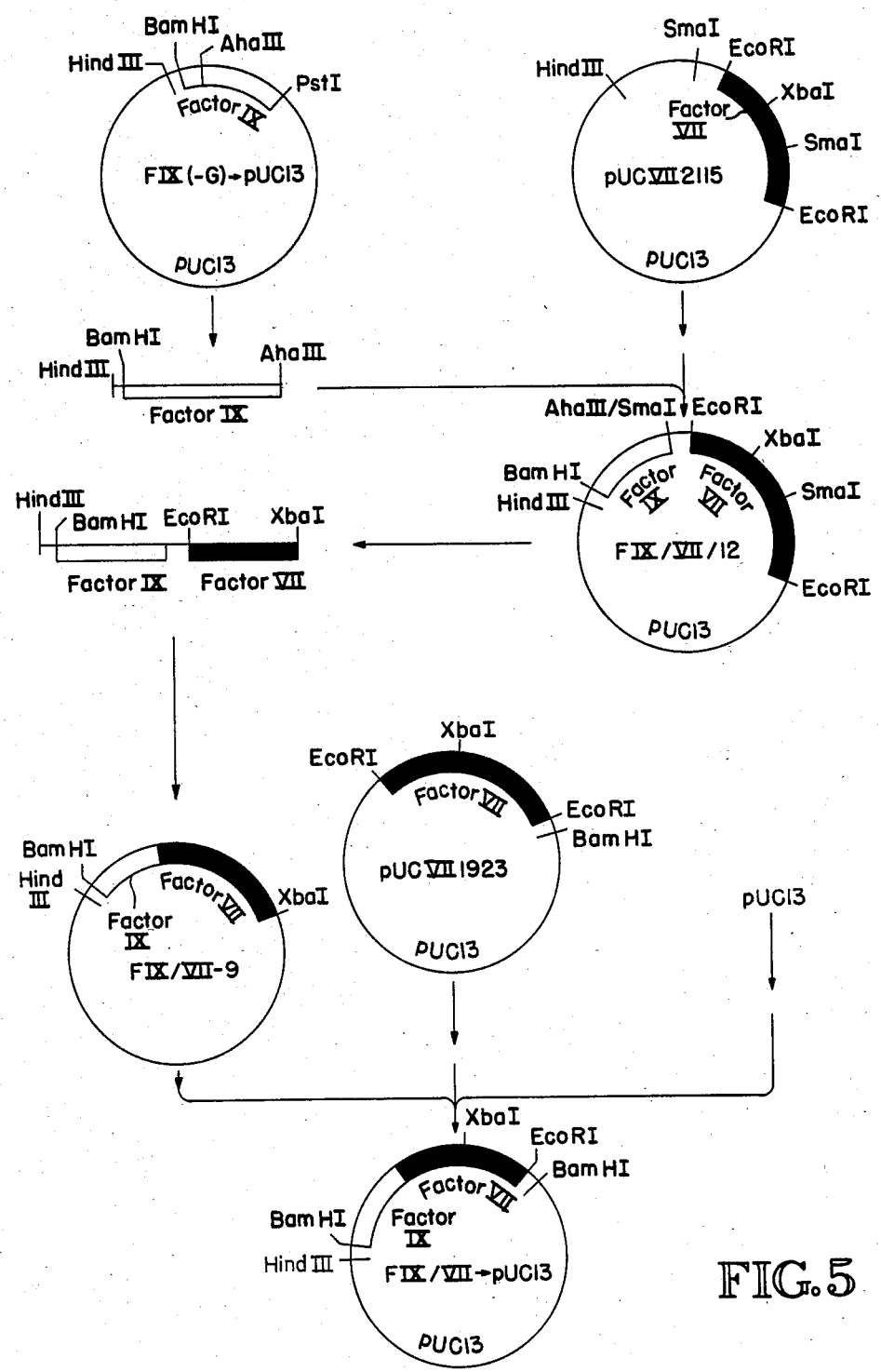
FIG. 5 illustrates the construction of a plasmid containing a coding sequence for a Factor IX/Factor VII fusion protein.

The Factor IX-consensus sequence hybrids (either mini or maxi) were joined to the 5' portion of the Factor VII cDNA and the vector pUC13 in a three-part ligation (FIGS. 4 and 5). The vector fragment was produced by digesting 6 ug of pUC13 with 10 units each of Xba I and Hind III in Hind III buffer containing RNase A (400 ng/ul). The mini-FIX-FVII fragment was produced by digesting 2 ug of pM7200(-C) with 10 units each of Hind III and Eco RI as above. The maxi-FIX-FVII fragment was similarly prepared from pM7100(-C). The 5' portion of the Factor VII cDNA was prepared from a plasmid (pUCG705) comprising the Eco RI-Xba I 5' fragment of pUCVII2115 subcloned into pUC13 by digestion with Xba I and Eco RI. Digests were run at 37° C. for 2 hours and the products were separated by electrophoresis on a 1.5% agarose gel. The desired fragments were electro-eluted, extracted with phenol/CHCl₃ and CHCl₃, and precipitated with ethanol. The three fragments, pUC13/Xba I-Hind III, Factor IX-Factor VII (mini or maxi)/Hind III-Eco RI, and 5' Factor VII/Eco RI-Xba I were then ligated in 20 ul of ligase buffer containing 2 ul 20 mM ATP and 0.9 unit T₄ DNA ligase overnight at 4° C. Colonies were screened by restriction analysis with Hind III and Xba I. The recombinant plasmids containing the mini- and maxi-FIX-FVII sequences were designated pM7200 and pM7100, respectively (FIG. 4).

Due to the linker addition used in producing the Factor VII cDNA, modifications had to be made in the fusion sequences to generate correct in frame coding sequences. Both mini- and maxi-fusions contain an Eco RI site at the junction between the Factor IX-consensus sequence hybrid and the Factor VII cDNa which is an artifact of the cDNA cloning process. In addition, the mini-fusion requires the addition of a C to change the sequence at the Hae III site from 5'AGGCCA3' to 5'AGGCCCA3' and establish the correct reading frame downstream of this sequence. These corrections were made by oligonucleotide-directed site specific mutagenesis, essentially as described for the two-primer method by Zoller and Smith (*Manual for Advanced Techniques in Molecular Cloning Course,* Cold Spring Harbor Laboratory, 1983). The mini-FIX-FVII fragment was removed from pM7200 by digestion with Hind III and Xba I and inserted into M13mpl9. The maxi-FIX-FVII fragment was purified from pM7100 and subcloned in a similar manner. The mutagenic primers ZC333 and ZC336 (see Table 1) were used for removal of the Eco RI site and the base insertion, respectively. In each case, the universal primer ZC87 was used as the second primer. The mutagenic primers were phosphorylated by combining 40 pmoles of primer and 60 pmoles ATP with 1 unit of $T_4$ DNA kinase overnight at 60° C. To remove the Eco RI site from the maxi-FIX-FVII hybrid, 1 ug of the M13 single-stranded template was combined with 20 pmoles each ZC333 and ZC87 in a total volume of 10 ul. The primers were annealed to the template for 10 minutes at 65° C., cooled to room temperature for 5 minutes, then placed on ice for 5 minutes. The primers were extended using DNA polymerase I (Klenow fragment). To remove the Eco RI site and correct the reading frame in the mini-FIX-FVII hybrid, 1 ug of the appropriate M13 single-stranded template was combined with 20 pmoles each ZC333, ZC336 and ZC87. Annealing and primer extension reactions were carried out as described above. Plaque lifts were screened with $^{32}$P-labeled primer (ZC333 or ZC336) at 60° C. and sequences confirmed by dideoxy sequencing. The resultant constructs, comprising the maxi- and mini-FIX-FVII sequences, were designated pM7111 and pM7211, respectively.

The consensus sequence contains several regions which do not conform to the protein sequence data obtained for Factor VII (FIG. 2). In order to produce a sequence which encodes a polypeptide with greater homology to the amino-terminal portion of Factor VII, the consensus sequence was altered by oligonucleotide-directed site-specific mutagenesis. The changes made were the insertion of Leu at position 8, substitution of Ile for Lys at position 18 (numbers refer to the amino acid position after the insertion at position 8), Asn for Ala at position 26, and the sequence Ala-Ser-Asp for Gly-Leu-Asn at positions 32-34 (based on tentative amino acid sequence data).

The sequence changes at positions 8 and 18 were made using pM7111 (sense strand) as template. Primers ZC352 (5'CCC AGG TCT CAG CTC CTC CAG3') and ZC353 (5'CTG CTC CTC CTT ACA CTC TCT3') were annealed to the template and extended as described above. The resultant phage clone was designated pM7114. The sequence of the insert in pM7114 was confirmed by dideoxy sequencing.

In a similar manner, the changes at positions 26-34 were made on the pM7114 template (sense strand) using the mutagenic primer ZC366 (5'CAG CTT CGT CCT GTT CAG GCC CTC GAA GAT CTC GCG GGC CTC CTC GAA3') and ZC87 (Table 1) as second primer. The resultant construct was designated pM7115. The sequence of the entire 550 bp insert in the M13 vector was determined by dideoxy sequencing and found to be correct.

EXAMPLE 5

Construction of Factor IX-Factor VII cDNA fusion

The Factor IX-Factor VII cDNA fusion was prepared using Factor IX cDNA obtained from a human liver cDNA library as described by Kurachi and Davie (ibid) and the Factor VII cDNA sequence described in Example 1.

The fusion point chosen for the hybrid protein was between amino acid +38 (threonine) of Factor IX and the first lysine encoded by the Factor VII cDNA sequence. Such a protein would be encoded by a sequence consisting of the first 252 bp of the Factor IX cDNA sequence and all of the pUCVII2115 Factor VII cDNA sequence except the first two codons. To construct this hybrid sequence, the Factor IX sequence was first fused to pUCVII2115 using convenient restriction sites. This fusion resulted in the plasmid FIX/VII/12 (described below) which contains the first 310 bp of the Factor IX cDNA joined to the entire Factor VII cDNA sequence. To achieve the precise junction desired for the hybride protein, the intervening base pairs were removed by oligonucleotide-directed mutagenesis.

Joining of the Factor IX cDNa sequence to Factor VII cDNA sequence was accomplished by ligating a 0.3 kb Hind III-Aha III fragment of FIX (—G)→pUC13 (Example 4) to a 4.7 kb Sma I-Hind III fragment from pUCVII2115 (FIG. 5). The Hind III-Aha III fragment was prepared by digesting 3 ug of FIX(—G)→pUC13 with 40 units of Hind III in 40 ul of medium salt buffer (Maniatis et al., ibid) at 37° C., 4 hours. The volume was then increased to 100 ul of medium salt buffer, and 5 units of Aha III were added and the 37° C. incubation continued for 18 hours. The DNA fragments were separated by electrophoresis in 1% agarose and the 0.3 kb band isolated as described above. A Sma I partial digestion of pUCVII2115 was obtained by incubating 3 ug of pUCVII2115 at 25° C. for 1 hour with 4.8 units of Sma I in a reaction volume of 30 ul. The reaction was stopped by a 15-minute incubation at 65° C. The sample was then extracted once with an equal volume of phenol and ethanol precipitated.

The precipitate was collected by a 10-minute microfuge spin, rinsed with 70% ethanol and air dried. The DNA was redissolved in 30 ul of medium salt buffer and digested with 30 units of Hind III at 37° C. for 3 hours. The DNA was subjected to electrophoresis in 0.7% agarose and the 4.7 kb Hind III-Sma I fragment isolated as described above. Equimolar amounts of the two fragments (0.048 pmoles) were ligated in a 10 ul reaction containing 50 mM Tris-HCl pH 7.5, 10 mM $MgCl_2$, 1 mM DTT, 1 mM ATP, and 3 units of $T_4$ DNA ligase at 14° C. for 3.5 hours and then used to transform competent E. coli RRI (ATCC 31343). The cells were grown on ampicillin plates and 12 of the resulting colonies were screened by restriction enzyme digestion for the presence of the desired plasmid construction. DNA from colony 12 (FIX/VII/12) gave the expected restriction enzyme digestion pattern and was used in the next step of the hybrid gene construction.

The oligonucleotide-directed mutagensis procedure was performed on a single-stranded DNA template. Thus, it was necessary to clone the fused Factor IX/-Factor VII sequences into M13mp19. To obtain a conveniently small DNA fragment, a 640 bp Hind III-Xba I fragment was isolated from FIX/VII/12. This fragment contains 310 bp of the 5' end of Factor IX cDNA and 330 bp of the Factor VII sequence. The vector was prepared by digesting 1 ug of M13mp19 RF DNA with 20 units of Hind III and 20 units of Xba I in 40 ul of medium salt buffer at 37° C. for 18 hours. The DNA was subjected to electrophoresis in 1.2% agarose and the linear 6.4 kb fragment isolated from the gel as described above. Five ug of FIX/VII/12 DNA was digested with 10 units of Xba I in 40 ul of medium salt buffer at 37° for 18 hours. Twenty units of Hind III were added and the digestion continued at 37° C. for an additional 7 hours. The resulting fragments were separated by electrophoresis in 1.2% agarose and the 640 bp fragment eluted as above. Ten ng of linearized M13mp19 and 1 ng of the 640 bp fragment were ligated at 14° C. for 1 hour and then used to transform competent *E. coli* JM101 (Messing, *Meth. in Enzymology*, ibid). The cells were plated with X-gal and IPTG (Messing, *Meth. in Enzymology*, ibid) *and eight light blue plaques were picked and used to infect* 2.5 ml cultures of *E. coli* JM103 at $A_{600}=0.3$. After 18 hours' growth at 37° C., the cells were harvested by centrifugation in a room temperature clinical centrifuge and 20 ul of the supernatant which contains the M13 phage was mixed with 10 ug/l ethidium bromide. By comparison with known standards, each of the eight clones had an insert of approximately the correct size. Single-stranded DNA was then prepared from 1.5 ml of the supernatants as described by Messing (*Meth. in Enzymology*, ibid). This construct was then sequenced by the dideoxy method using the oligonucleotide ZC87 as a primer to confirm that the insert junction was correct. One of the correct clones (#4) was used as a template in oligonucleotide-directed mutagenesis to produce a functional Factor IX-Factor VII fusion.

The oligonucleotide ZC249, a 20-mer consisting of 10 bp of the desired Factor IX sequence and 10 bp of the desired Factor VII sequence (Table 1) was used as the mutagenic primer. The oligonucleotide ZC87, which hybridizes to the M13mp19 sequence, was used as the second primer.

The mutagenesis procedure used was modified from that of Zoller and Smith (ibid). For the annealing reaction, 20 pmoles of ZC249 were phosphorylated by incubating overnight at 4° C. in 20 ul 60 mM Tris-HCl pH 8.0, 10 mM $MgCl_2$, 1 mM DTT, 1 mM ATP, 1 unit $T_4$ kinase. The reaction was stopped by incubation at 65° C. for 15 minutes, and the sample was lyophilized. One pmole of single-stranded clone #4 template and 20 pmole of ZC87 were added in 10 ul annealing buffer (200 mM Tris-HCl pH 7.5, 100 mM $MgCl_2$, 500 mM NaCl, 10 mM DTT). The sample was heated to 65° C. for 10 minutes, incubated at room temperature for 5 minutes, and then placed on ice. Ten ul of the following solution was prepared fresh and added to the sample: 20 mM Tris-HCl pH 7.5, 10 mM $MgCl_2$, 10 mM DTT, 1 mM dNTPs, 1 mM ATP, 0.15 units/ul $T_4$ DNA ligase, 0.25 units/ul *E. coli* DNA Polymerase I (Klenow fragment). The reaction was then incubated at 15° C. for 3 hours and the sample used to transform competent *E. coli* JM101 (Messing, *Meth. in Enzymology*, ibid).

The resulting plaques were lifted onto nitrocellulose and screened by hybridization to $^{32}P$-labeled ZC249. Dry BA85 filters (Schliecher & Schuell, 0.45 um) were laid onto the agar plate and the phage allowed to adsorb for 5 minutes. The filters were removed and allowed to dry for 5 minutes, placed on Whatman 3 MM paper, saturated in 0.5M NaOH, 1.5M NaCl for 5 minutes, air dried for 3 minutes, placed on Whatman paper, saturated in 1M Tris-HCl pH 8, 1.5M NaCl, for 5 minutes, and air dried for 3 minutes. The Tris-HCl step was repeated and the filters were rinsed in 100 ml 6×SSC for 2 minutes at room temperature. After air drying, the filters were baked at 80° C. for 2 hours and prehybridized at 47° C. ($T_m-4°$ of ZC249) overnight in 6.7×SSC pH 6.5, 2 mg/ml *E. coli* tRNA, and 0.2% (w/v) each BSA, Ficoll, and polyvinylpyrolidine.

After the prehybridization step, the filters were incubated with $2.5\times10^6$ cpm/filter of labeled ZC249 in the same SSC hybridization buffer at 47° C. overnight. Following hybridization, the filters were washed 3 times, 5-10 minutes each, at room temperature in 6×SSC and exposed to X-ray film. Putative positive plaques were replated and screened as above. Individual plaques were then picked, and single-stranded DNA was prepared and sequenced using ZC275 as a primer. The oligonucleotide ZC275 corresponds to a sequence 40 bp in the 5' direction of ZC249 on the same strand (Table 1).

Four positive plaques were identified. The entire insert in M13mp19 for one clone (FIX/VII-9) was sequenced by the dideoxy method using the oligonucleotides ZC87 and ZC275 and determined to be correct. The confirmed sequence is represented by bases 1-567 in FIG. 7. RF DNA from this clone was then used for the final step in the construction of the hybrid gene.

Three fragments were used to make the final construction: the 0.6 kb Hind III-Xba I fragment from FIX/VII-9 containing the fused IX/VII sequences; a 1.7 kb Xba I-Bam HI Factor VII cDNA fragment from pUCVII1923; and a 2.7 kb BAM HI-Hind III fragment of pUC13. Three ug of FIX/VII-9 (RF DNA) were digested at 37° C. for 6 hours with 45 units of Xba I in a volume of 50 ul. The DNA was precipitated with ethanol, resuspended and digested at 37° C. for 4 h with 50 units of Hind III. The sample was subjected to electrophoresis in 1% agarose and the 0.6 kb band electroeluted onto NA45 paper (Schliecher & Schuell). The DNA was eluted from the paper with 1.5M NaCl, 50 mM Tris-HCl pH 8, 1 mM EDTA, phenol extracted and precipitated with ethanol.

To obtain the remaining Factor VII cDNA sequence, 5 ug of pUCVII1923 was digested at 37° C. for 3 hours with 36 units of Xba I in 40 ul of medium salt buffer. Then 8 ul of 10x high salt buffer, 28 ul of $H_2O$, and 4 ul (40 units) of Bam HI were added and the reaction incubated at 37° C. for 3 hours. The DNA fragments were separated by electrophoresis in 1% agarose and the 1.7 kb fragment isolated as described above.

The vector fragment was prepared by digesting 1 ug of pUC13 with 10 units of Hind III in 20 ul of medium salt buffer at 37° C. for 1 hour. Two ul of 10x high salt buffer and 10 units of Bam HI were then added and the incubation continued for another 2 hours. The DNA was purified on a 1% agarose gel as described above.

Equimolar amounts (approximately 0.56 pmoles) of the three fragments were ligated at room temperature for 45 minutes in 10 ul of 50 mM Tris-HCl pH 7.5, 10 mM $MgCl_2$, 1 mM DTT, 1 mM ATP and 3 units $T_4$ DNA ligase. The reaction mixture was used to transform competent *E. coli* JM83. The cells were plated on medium containing 40 ug/ml ampicillin with 50 ul of 2% X-gal added to each plate. DNA was prepared from 7 white colonies and then screened by restriction enzyme digestion. One of the clones giving the correct pattern was designated FIX/VII→pUC13.

EXAMPLE 6

Expression of Biologically Active Factor VII Analogs

The mammalian cell expression vector pD2 was chosen for expression of the FIX/VII gene in transfected animal cells. It was constructed from plasmid pDHFR-III (Berkner and Sharp, *Nuc. Acids Res.* 13: 841-857, 1985) in the following manner. The Pst I site abutting the DHFR cDNA in pDHFR III was converted to a BAM HI site by conventional linkering (Scheller, R. H., Dickerson, R. E., Boyer, H. W., Riggs, A. D., and Itakura, K., *Science* 196: 177–180, 1977). The pDHFR III DNA was incubated with 10 mM Tris pH 7.6, 6 mM β-MSH, 6 mM NaCl, 10 mM MgCl$_2$ and 2.5 units Pst I for 10 minutes at 37° C., followed by phenol extraction and ethanol precipitation. The Pst I cohesive termini were blunt ended using T$_4$ DNA polymerase. After phenol extraction and dialysis against 10 mM Tris pH 8.0, 1 mM EDTA, 0.3M NaCl, the DNA was ethanol precipitated. The DNA was resuspended in 20 ul 1.4 mM ATP, 50 mM Tris pH 7.6, 10 mM MgCl$_2$, 1 mM dithiothreitol and then incubated with 5 ng of T$_4$ polynucleotide kinase-treated Bam HI linkers (New England Biolabs) and 200 units of T$_4$ polynucleotide ligase for 12 hours at 12° C., followed by phenol extraction and ethanol precipitation. The DNA was digested with 90 units of Bam HI at 37° C. for 1 hour, followed by electrophoresis through a 1.4% agarose gel. The 4.9 kb DNA fragment (corresponding to pDHFR III DNA lacking the DHFR cDNA and SV40 polyadenylation signal) was electro-eluted and recircularized with polynucleotide ligase and then transfected into *E. coli* HB101. Ampicillin-sensitive colonies were screened by rapid prep analysis (Birnboim, H. C., and Doly, J., *Nucleic Acids Research* 7: 1513–1523, 1979) and the correct clone was grown up to generate a large-scale plasmid DNA preparation.

The resultant plasmid was cleaved with 20 units Bam HI and treated with 2.5 ug calf intestinal phosphatase and electrophoresed on a 1.4% agarose gel. Twenty-five ug of pSV40 (a clone of SV40 DNA inserted into the Bam HI site of pBR322) were digested with 25 units of Bcl I for 1 hour at 50° C., followed by the addition of 25 units of Bam HI, and the incubation continued for 1 hour at 37° C. This DNA was then electrophoresed on a 1.4% agarose gel. The Bam HI-cut vector (i.e., that lacking the polyadenylation signal) was joined to the SV40 DNA fragment (0.14 to 0.19 map units [Tooze, J., ed., "DNA Tumor Viruses, Molecular Biology of Tumor Viruses"]) containing the late polyadenylation signal by incubating the gel-purified fragments (0.1 ug each) in 20 ul 50 mM Tris pH 7.6, 10 mM MgCl$_2$, 1 mM dithiothreitol, 1.4 mM ATP and 100 units T$_4$ polynucleotide ligase for 4 hours at 12° C., followed by transformation into *E. coli* RR1. Positive colonies were identified by rapid prep analysis, and a large-scale plasmid preparation of the correct DNA, pD2, was prepared.

Figure 6:
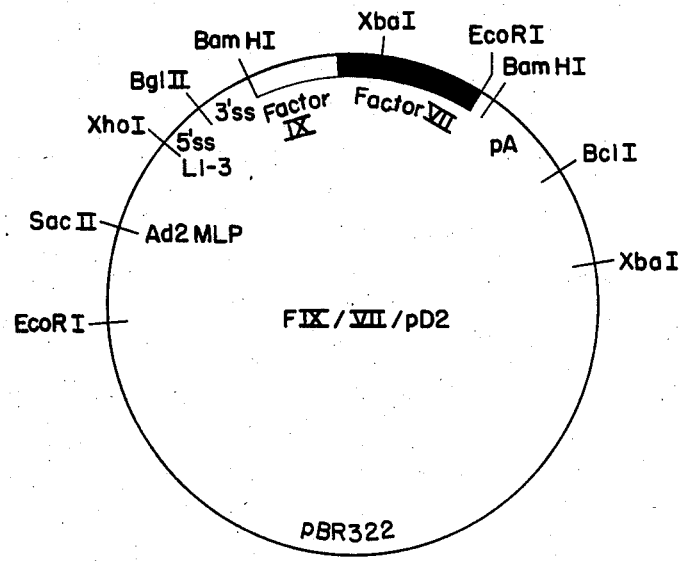
FIG. 6 illustrates the expression vector FIX/-VII/pD2. Symbols usee are Ad2 MLP, the major late promoter from adenovirus 2; L1-3, the adenovirus 2 tripartite leader sequence; 5'ss, 5' splice site; 3'ss, 3' splice site; and pA, the late polyadenylation signal from SV40.

To make the Factor IX/VII expression construction, 1 ug of pD2 was digested at 37° C. for 1 hour with 20 units of Bam HI in 20 ul of high salt buffer. Twenty ul of 10 mM Tris-HCl pH 8, 1 mM EDTA and 0.1 unit of calf alkaline phosphatase (Boeringer) were then added. The reaction was incubated at 37° C. for 1 hour and stopped by heating to 75° C. for 10 minutes. Ten ug of FIX/VII→pUC13 was digested at 37° C. for 2 hours with 150 units of Bam HI in 150 ul of high salt buffer. The DNA fragments were separated by electrophoresis in 1.2% agarose and the 2.3 kb fragment was isolated. Equimolar amounts (0.015 pmoles) of the 2.3 kb Bam HI fragment and the pD2 vector fragment were ligated at 14° C. for 2.5 hours as above. The reaction mixture was used to transform *E. coli* RR1 cells, which were then plated on medium containing 10 ug/ml ampicillin. Plasmid DNA was prepared from 12 of the resulting colonies and screened by restriction enzyme digestion. One of the clones with the correct enzyme digestion pattern was designated FIX/VII/pD2 (FIG. 6). *E. coli* RR1 transformed with FIX/VII/pD2 has been deposited with ATCC under accession number 53068.

The procedure used to transfect baby hamster kidney (BHK) cells (available from American Type Culture Collection, accession number CCL10) with FIX/VII/pD2 was similar to published methods (for example, Wigler et al., *Cell* 14: 725, 1978; Corsaro and Pearson, *Somatic Cell Genetics* 7: 603, 1981; Graham and Van der Eb, *Virology* 52: 456, 1973). The BHK cells were grown at 37° C., 5% CO$_2$, in Dulbecco's media (plus 10% heat-inactivated fetal calf serum and supplemented with glutamine and penicillin-streptomycin) in 60 mm tissue culture Petri dishes to a confluency of 20%. A total of 10 ug DNA was used to transfect one 60 mm dish: 3.75 ug of FIX/VII/pD2, 1.25 ug of pKO-neo (Southern and Berg, *J. Mol. Appl. Genet.* 1: 327–341, 1982) and 5 ug of salmon sperm DNA. The DNAs were precipitated in 0.3M NaOAc, 75% ethanol, rinsed with 70% ethanol and redissolved in 20 ul 10 mM Tris-HCl pH 8, 1 mM EDTA. The DNA was combined with 440 ul H$_2$O and 500 ul of 280 mM NaCl, 1.5 mM NaHPO$_4$, 12 mM dextrose, 50 mM HEPES pH 7.12. Sixty ul of 2M CaCl$_2$ were added dropwise to the above mixture and the solution let stand at room temperature for 30 minutes. The solution was then added to the cells and the cells returned to 37° C. for 4 hours. The medium was removed and 5 ml of 20% DMSO in Dulbecco's with serum was added for 2 minutes at room temperature. The dish was then washed rapidly with 2 changes of medium and incubated in fresh medium overnight. Twenty-four hours after the DNA was added, the medium was removed and selective medium added (10 mg/ml of G418, 498 ug/mg, Gibco, in Dulbecco's with serum). After 10 and 13 days, individual clones, representing cells that had incorporated the pKO-neo gene and were thus resistant to G418, were transferred to 96-well (or 24-well) plates and grown up for protein assays.

Cells were grown in Dulbecco's plus 10% fetal calf serum containing 5 ug/ml vitamin K (Phytonadione, Merck). The medium was separated from the cells and cellular debris by centrifugation, and assayed for Factor VII polypeptide (by ELISA) and for biological activity. The cells were removed from the plates with trypsin, washed with fresh medium, centrifuged, and frozen at −20° C. the cell pellets were then thawed in PBS, pelleted, and resuspended in PBS containing 0.25% Triton X-100. Samples were diluted and assayed for polypeptide and activity.

The ELISA for Factor VII was done as follows. Two hundred microliters of a monoclonal antibody against human Factor VII (5 ul/ml in 0.1M Na$_2$CO$_3$ pH 9.6) were incubated in each well of a 96-well microtiter plate 2 hours at 37° C. The wells were then incubated with 220 ul of 1% bovine serum albumin (BSA) and 0.05% Tween 20 in PBS pH 7.2 2 hours at 37° C. The plates were rinsed with H$_2$O, air dried, and stored at 4° C. To assay samples, 200 ul samples were incubated 1 hour at room temperature in the antibody-coated wells. The wells were then rinsed four times with 200 ul PBS containing 0.05% Tween 20. The wells were then incubated for 1 hour at room temperature with 200 ul of an IgG fraction of rabbit polyclonal antiserum against Factor VII (5 ug/ml in PBS containing 1% BSA and 0.05% Tween 20). This was followed by incubatin with goat anti-rabbit IgG coupled to alkaline phosphatase. The wells were then rinsed four times with PBS containing 0.05% Tween 20. To the wells were added 200 ul p-nitrophenyl phosphate (30 mg) dissolved in diethanolamine buffer (96 ml per liter) pH 9.8 containing 56 mg/l MgCl$_2$. The enzyme reaction was done at 37° C. and the development of a yellow color was monitored at 405 nm using an ELISA plate reader. Results obtained for cell media are given in Table 3.

Factor VII biological activity was assayed by the one-stage clotting assay described by Quick (*Hemorragic Disease and Thrombosis*, 2nd ed., Leat Febiger, Philadelphia, 1966). Results obtained for cell media are given in Table 3.

TABLE 3

| Day | Cells/ml (×10$^{-4}$) | Factor VII polypeptide ng/ml | Factor VII activity (ng/ml) |
|---|---|---|---|
| 1 | 2.9 2.7 | 25 | 6.0 |
| 2 | 1.9 2.8 | 47 | 15.9 |
| 3 | 1.96 2.26 | 160 | 93 |
| 4 | 4.71 4.14 | 550 | 300 |
| 5 | 8.79 11.28 | 725 | 531 |
| 6 | 5.1 8.4 | 975 | 600 |

EXAMPLE 7

Expression of Factor IX

Fourteen ug of FIX(-G)→pUC13 were digested with 30 units of Bam HI in 30 ul of high salt buffer for 3 hours at 37° C. The DNA was then subjected to electrophoresis in 1% agarose and the 1.4 kb band containing the Factor IX sequence was isolated from the gel.

Three ug of the vector pD2 were digested with 30 units of Bam HI in 30 ul high salt buffer for 3 hours at 37° C. The DNA was subjected to electrophoresis in 1% agarose and the linear 1.5 kb fragment isolated. The DNA was then treated with 0.12 units calf alkaline phosphatase in 30 ul of 10 mM Tris-HCl pH 8, 1 mM EDTA for 30 minutes at 37° C. The salt was adjusted to 0.3M NaOAc and the sample extracted twice with phenol, once with chloroform and the DNA was ethanol precipitated. The pellet was rinsed in 70% ethanol, dried and redissolved in 20 ul 10 mM Tris-HCl pH 8, 1 mM EDTA. Equimolar amounts (0.02 pmoles) of the two fragments were ligated with 10 units of T$_4$ DNA ligase as described above. The reaction mixture was used to transform *E. coli* RR1 cells. DNA from twelve of the resulting ampicillin-resistant colonies was screened by restriction enzyme digestion. One of the clones with the 1.4 kb fragment inserted in the correct orientation was designated as FIX(-G)/pD2. *E. coli* RR1 transformed with FIX(-G)/pD2 has been deposited with ATCC under accession number 53067.

BHK cells were co-transfected with FIX(-G)/pD2 and pKO-neo as described above. Drug-resistant cells were selected and prepared for ELISA and activity assay as described in Example 6.

The assay for biological activity is based on the ability of Factor IX to reduce the clotting time of plasma from Factor IX-deficient patients to normal. It was done as described by Proctor and Rapaport (*Amer. J. Clin. Path.* 36: 212, 1961). Results are shown in Table 4.

TABLE 4

| Day | Cells/ml (×10$^{-4}$) | Factor IX polypeptide (ng/ml) supernatant | Factor IX polypeptide (ng/ml) pellet | Factor IX activity (ng/ml) in supernatant | % active protein in supernatant |
|---|---|---|---|---|---|
| 1 | 1.65 | — | — | — | — |
| 2 | 2.66 | 57 45 | 20 20 | 27 24 | 50% |
| 3 | 9.69 | 150 120 | 60 60 | 72 84 | 58% |
| 4 | 14.79 | 475 225 | 160 140 | 198 150 | 50% |
| 5 | 50.85 | 875 1000 | 250 260 | 408 438 | 45% |

The amount of Factor IX polypeptide was determined by ELISA essentially as described in Example 6 using polyclonal rabbit antisera to Factor IX. Following the incubation of the wells with the Factor IX-containing samples, the wells were rinsed and incubated 1 hour at room temperature with 200 ul of affinity purified rabbit polyclonal anti-Factor IX conjugated to alkaline phosphatase diluted 1:1000 in PBS containing 1% BSA and 0.05% Tween 20. The wells are then rinsed four times with PBS containing 0.05% Tween 20, and enzyme substrate was added as above. Incubations were run at 4° C. overnight or 37° C. for 2 hours.

As shown in Table 4, 70%-80% of the Factor IX polypeptide is secreted into the media, and about 50% of this is biologically active. No Factor IX activity was detected in the cell pellets.

Highest levels of activity were achieved by supplementing the cell culture medium with vitamin K (phytonadione, Merck) at concentrations of 1-10 mg/ml.

Several additional analyses were performed to demonstrate that the cells were secreting authentic Factor IX. Samples containing Factor IX activity according to the above assay were incubated with Factor VIII-deficient plasma but did not affect the clotting time, indicating that the activity was due to authentic Factor IX rather than a non-specific clotting agent. This conclusion was further verified by depletion of Factor IX activity from the samples with a specific antibody. Ninety-seven to ninety-eight percent of the Factor IX activity was immunoprecipitated from cell supernatants with a rabbit polyclonal antibody against Factor IX. This antibody also precipitated over 99% of the Factor IX activity from normal plasma. No Factor IX activity was removed from the supernatants by rabbit polyclonal antibody to erythropoietin.

EXAMPLE 8

Construction of an expression vector for Factor VII

An expression vector comprising the synthetic Factor VII 5' coding region joined to the partial Factor VII cDNA was constructed. The vector, designated pM7135, was generated by inserting the Factor IX leader—5' Factor VII sequence from pM7115 and the 3' Factor VII sequence from FIX/VII/pD2 into plasmid pD3, which comprises the SV40 enhancer, and the adenovirus 2 major late promoter and tripartite leader.

Plasmid pD3 was generated from plasmid pDHFRIII. The Pst I site immediately upstream from the DHFR sequence in pDHFRIII was converted to a BcL I site by digesting 10 ug of plasmid with 5 units of Pst I for 10' at 37° C. in 100 ul buffer A (10 mM Tris pH 8, 10 mM MgCl$_2$, 6 mM NaCl, 7 mM β-MSH). The DNA was phenol extracted, EtOH precipitated, and resuspended in 40 ul buffer B (50 mM Tris pH 8, 7 mM MgCl$_2$, 7 mM β-MSH) containing 10 mM dCTP and 16 units T4 DNA polymerase and incubated at 12° C. for 60 minutes. Following EtOH precipitation, the DNA was ligated to 2.5 ug kinased Bcl I linkers in 14 ul buffer C (10 mM Tris pH 8, 10 mM MgCl$_2$, 1 mM DTT, 1.4 mM ATP) containing 400 units T4 polynucleotide ligase for 12 hours at 12° C. Following phenol extraction and EtOH precipitation, the DNA was resuspended in 120 ul buffer D (75 mM KCl, 6 mM Tris pH 7.5, 10 mM MgCl$_2$, 1 mM DTT), digested with 80 units Bcl I for 60 minutes at 50° C., then electrophoresed through agarose. Form III plasmid DNA (10 ug) was isolated from the gel, and ligated in 10 ul buffer C containing 50 units T4 polynucleotide ligase for 2 hours at 12° C., and used to transform E. coli HB101. Positive colonies were identified by rapid DNA preparation analysis, and plasmid DNA (designated pDHFR') prepared from positive colonies was transformed into dAM⁻ E. coli.

Plasmid pD2' was then generated by cleaving pDHFR' (15 ug) and pSV40 (25 ug) in 100 ul buffer D with 25 units Bcl I for 60 minutes at 50° C., followed by the addition of 50 units Bam HI and additional incubation at 37° C. for 60 minutes. DNA fragments were resolved by agarose gel electrophoresis, and the 4.9 kb pDHFR' fragment and 0.2 kb SV40 fragment were isolated. These fragments (200 ng pDHFR' DNA and 100 ng SV40 DNA) were incubated in 10 ul buffer C containing 100 units T4 polynucleotide ligase for 4 hours at 12° C., and the resulting construct (pD2') used to transform E. coli RRI.

Plasmid pD2' was modified by deleting the "poison" sequences in the pBr 322 region (Lusky and Botcham, Nature 293: 79–81, 1981). Plasmids pD2' (6.6 ug) and pML-1 (Lusky and Botcham, ibid) (4 ug) were incubated in 50 ul buffer A with 10 units each Eco RI and Nru I for 2 hours at 37° C., followed by agarose gel electrophoresis. The 1.7 kb pD2' fragment and 1.8 kb pML-1 fragment were isolated and ligated together (50 ng each) in 20 ul buffer C containing 100 units T4 polynucleotide ligase for 2 hours at 12° C., followed by transformation into E. coli HB101. Colonies containing the desired construct (designated Δ pD2) were identified by rapid preparation analysis. Ten ug of ΔpD2 were then digested with 20 units each Eco RI and Bgl II, in 50 ul buffer A for 2 hours at 37° C. The DNA was electrophoresed through agarose, and the desired 2.8 kb fragment (fragment C) comprising the pBR322, 3' splice site and poly A sequences was isolated.

To generate the remaining fragments used in constructing pD3, pDHFRIII was modified to convert the Sac II (Sst II) site into either a Hind III or Kpn I site. Ten ug pDHFRIII were digested with 20 units Sst II for 2 hours at 37° C., followed by phenol extraction and ethanol precipitation. Resuspended DNA was incubated in 100 ul buffer B containing 10 mM dCTP and 16 units T4 DNA polymerase for 60 minutes at 12° C., phenol extracted, dialyzed, and ethanol precipitated. DNA (5 ug) was ligated with 50 ng kinased Hind III or Kpn I linkers in 20 ul buffer C containing 400 units T4 DNA ligase for 10 hours at 12° C., phenol extracted, and ethanol precipitated. After resuspension in 50 ul buffer A, the resultant plasmids were digested with 50 units Hind III or Kpn I, as appropriate, and electrophoresed through agarose. Gel-isolated DNA (250 ng) was ligated in 30 ul buffer C containing 400 units T4 DNA ligase for 4 hours at 12° C. and used to transform E. coli RRI. The resultant plasmids were designated pDHFRIII (Hind III) and pDHFRIII (Kpn I). A 700 bp Kpn I-Bgl II fragment (fragment A) was then purified from pDHFRIII (Kpn I) by digestion with Bgl II and Kpn I followed by agarose gel electrophoresis.

The SV40 enhancer sequence was inserted into pDHFRIII (Hind III) as follows: 50 ug SV40 DNA was incubated in 120 ul buffer A with 50 units Hind III for 2 hours at 37° C., and the Hind III C SV40 fragment (5089–968 bp) was gel purified. Plasmid pDHFRIII (Hind III) (10 ug) was treated with 250 ng calf intestinal phosphatase for 1 hour at 37° C., phenol extracted and ethanol precipitated. The linearized plasmid (50 ng) was ligated with 250 ng Hind III C SV40 in 16 ul buffer C for 3 hours at 12° C., using 200 units T4 polynucleotide ligase, and transformed into E. coli HB101. A 700 base pair Eco RI-Kpn I fragment (fragment B) was then isolated from this plasmid.

For the final construction of pD3, fragments A and B (50 ng each) were ligated with 10 ng fragment C with 200 units T4 polynucleotide ligase for 4 hours at 12° C., followed by transfection of E. coli RRI. Positive colonies were detected by rapid preparation analysis and a large-scale preparation of pD 3 was made.

Figure 8:
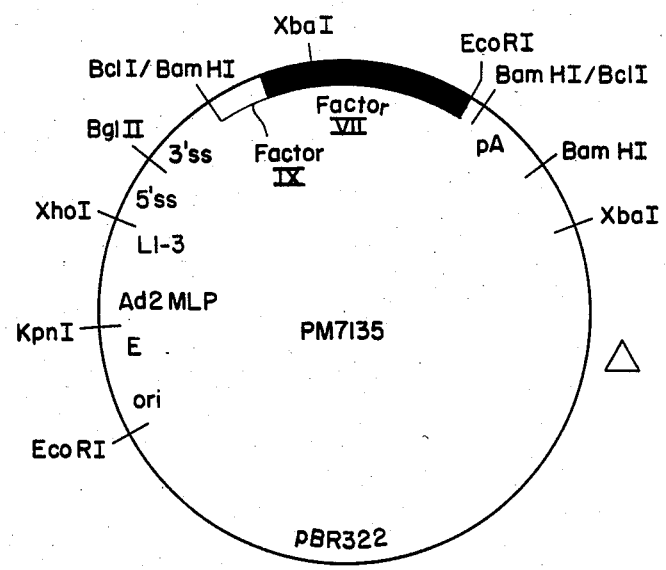
FIG. 8 illustrates expression vector pM7135. Symbols used are E, the SV40 enhancer; ori, the 0–1 map units Ad 5; pA, the early polyadenylation signal from SV40; Δ, the deletion region of the pBR322 "poison" sequences; and other symbols as described for FIG. 6.
Figure 9:
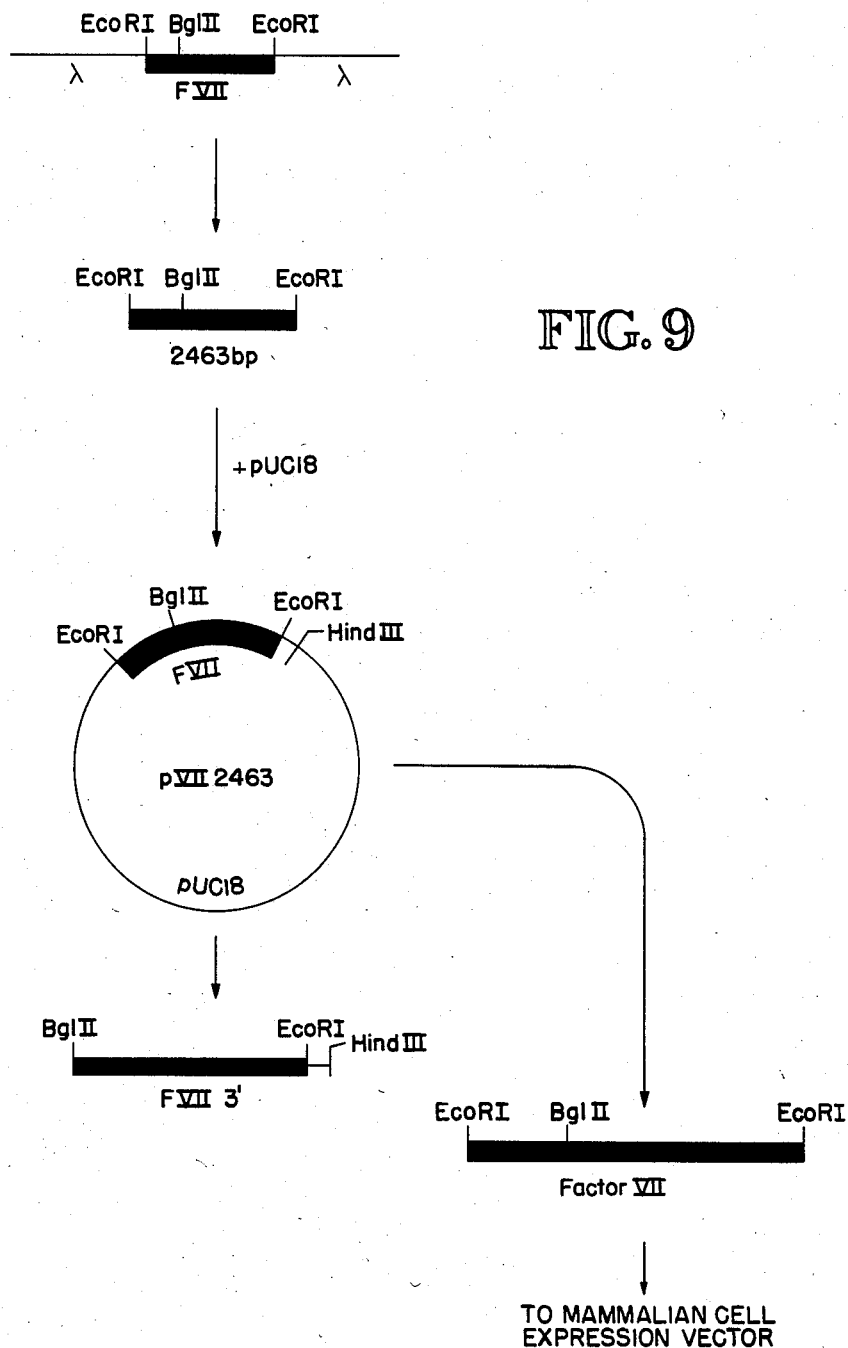
FIG. 9 illustrates the subcloning of the 2463bp Factor VII cDNA.
Figure 10:
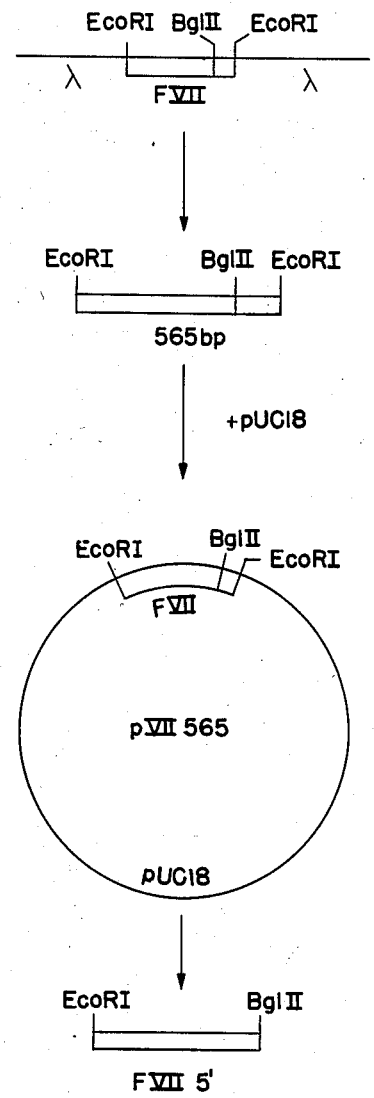
FIG. 10 illustrates the subcloning of the 565bp Factor VII cDNA.
Figure 11:
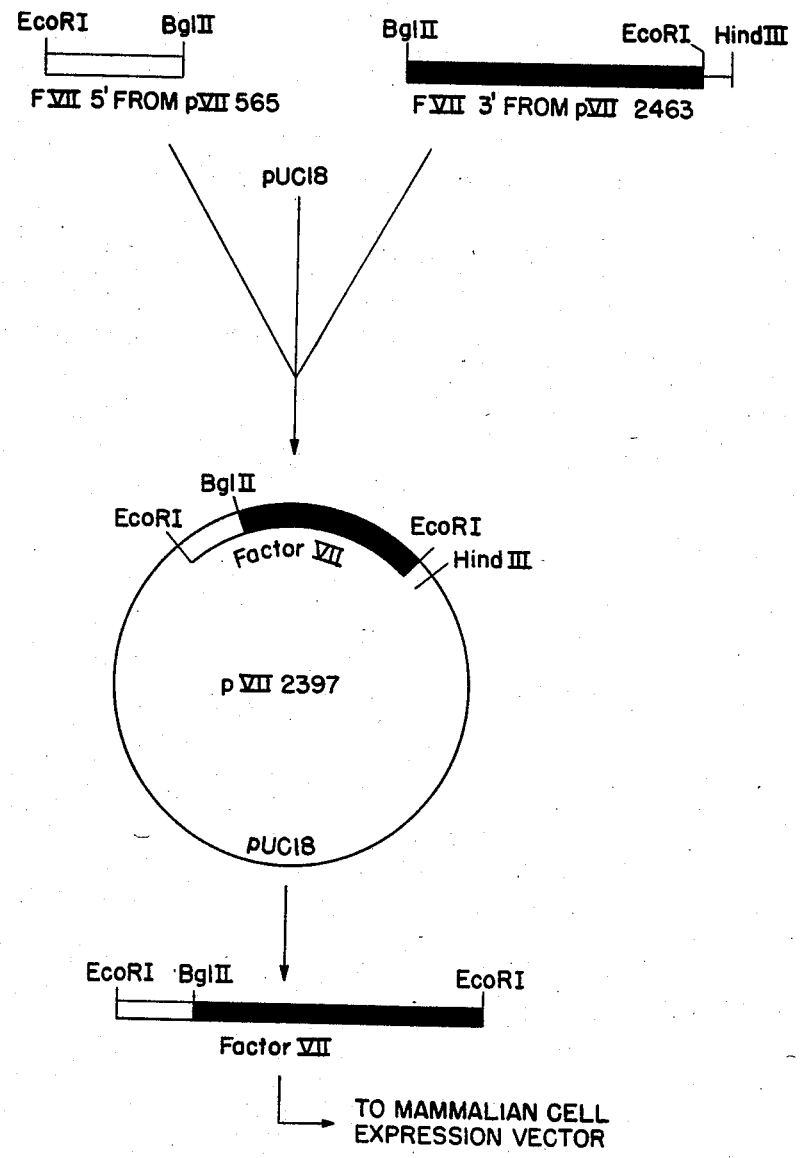
FIG. 11 illustrates the joining of the 5' end of pVII565 and the 3' portion of pVII2463 in pUC18 to generate pVII2397.

Expression vector pM7135 was then constructed. The replicative form of pM7115 was digested with Bam HI and Xba I and the 550 base pair fragment comprising the Factor IX leader and 5' Factor VII sequence was gel purified. Plasmid FIX/VII/pD2 was digested with Xba I and Bam HI and the 1700 bp fragment comprising the 3' portion of the Factor VII cDNA was gel purified. Plasmid pD3 was digested with Bcl I, treated with calf alkaline phosphatase, and the three fragments joined in a triple ligation. The resultant constructs were screened for the presence of a 2000 base pair Xba I fragment. A plasmid having the correct orientation was selected and designated pM7135 (FIG. 8).

EXAMPLE 9

Expression of Factor VII From cDNA Clones

In order to express Factor VII cDNA containing a Factor VII leader, DNA from λVII2463 or λVII565 and λVII2463 was cloned into an expression vector containing the Ad2 major late promoter, SV40 enhancer sequences, the Ad2 tripartite leader, a splice set, and the SV40 polyadenylation signal. This vector was adapted so that it contains a unique EcoRI sequence as the site of cDNA insertion. The expression of sequences from λVII2463, which encodes a 60 amino acid leader, and from λVII565 and λVII2463, which lacks the codons for amino acids from −18 to −39 and thus encodes a leader 38 amino acids in length, were evaluated. Because the structure of the Factor VII leader has only been identified by cDNA cloning, and because of the ambiguity generated by having obtained two different 5'-terminal cDNAs, the inventors also constructed a genomic-cDNA Factor VII sequence. The 3' portion of λVII2463 (from the Bgl II site in exon 2, to the EcoRI site linkered 3' to the poly(A) tail) was adjoined to a subgenomic fragment of clone 7 ml, that encoding exons 1a, 1b and the remainder of exon 2. This subgenomic fragment, reconstructed as an EcoRI-BgIII 4.4 Kb fragment, was adjoined to the λVII2463 cDNA and cloned into a mammalian expression vector.

Briefly, in order to construct the subclones, the Factor VII cDNA EcoRI fragment of λVII2463 was cloned into the EcoRI site of pUC18, and designated pVII2463. Similarly, the EcoRI cDNA insert of λVII565 was subcloned into pUC18, and designated pVII565. A hybrid between the 5' portion of the Factor VII sequence of clone pVII565 and the 3' segment of Factor VII DNA of pVII2463 was constructed by cloning the 5'-most EcoRI-Bgl II Factor VII fragment of pVII565 and the Bgl II-Hind III Factor VII fragment (Hind III site in polylinker of pVII2463) of pVII2463 into pUC 18 digested with EcoRI and Hind III. This construct was designated pVII2397. The inserts of pVII2463 and pVII2397 were removed by EcoRI digestion and gel purified for insertion into mammalian expression vectors as described below.

A. Expression of full-length Factor VII cDNA.

The expression of Factor VII was achieved in the vector pDX. This vector was derived from pD3 (described in Example 8 above) and pD3', a vector identical to pD3 except that the SV40 polyadenylation signal (i.e. the SV40 Bam HI [2533 bp] to BclI [2700 bp] fragment) is in the late orientation. Thus, pD3' contains a Bam HI site as the site of gene insertion.

Figure 12:
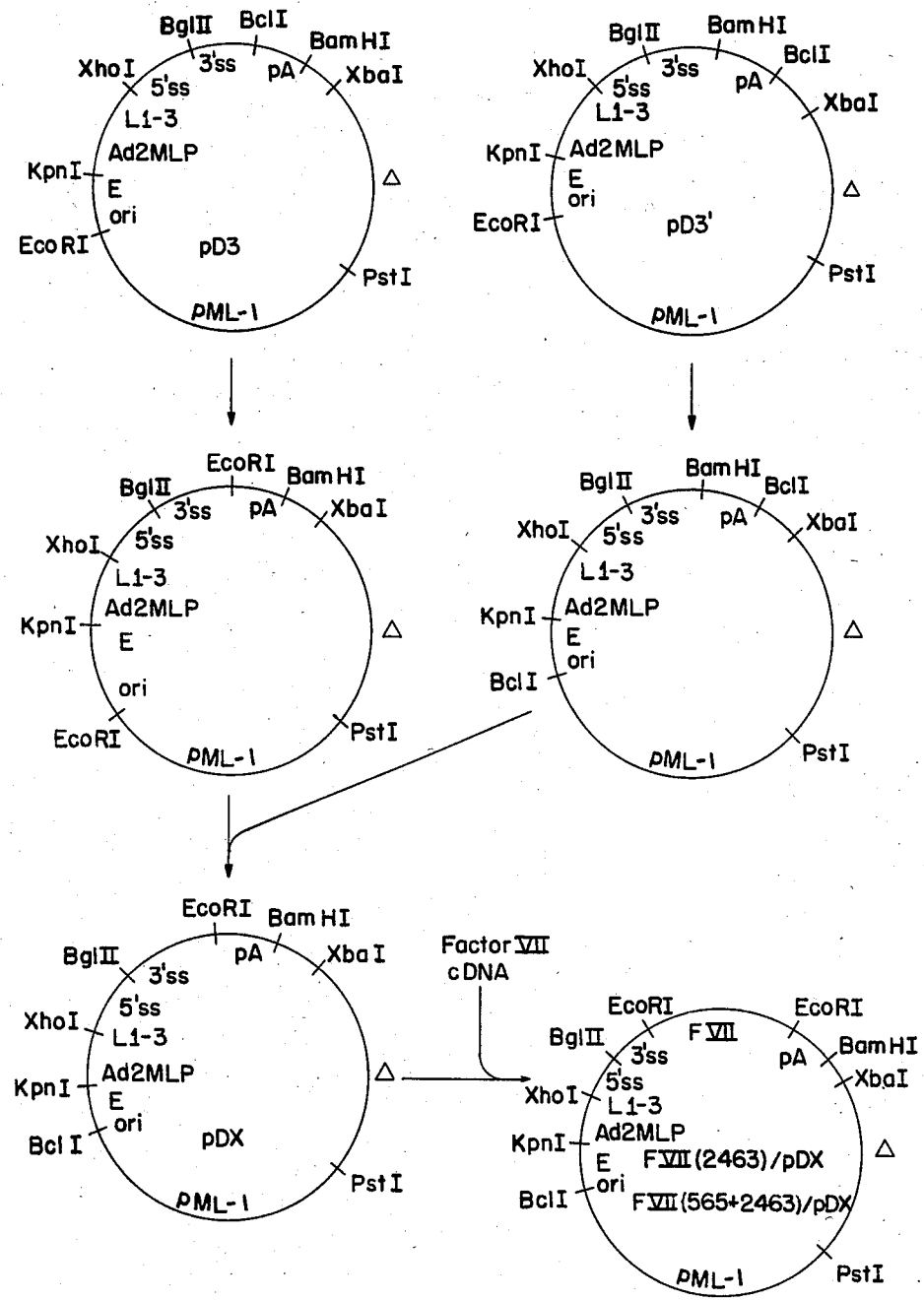
FIG. 12 illustrates the construction of the expression plasmids FVII(2463)/pDX and FVI1(565+2463)/pDX. pA denotes the polyadenylation signal from SV40 in early or late orientation, as described in Example 9. Other symbols are as described for FIG. 8.

To generate pDX, the EcoRI site in pD3' was converted to a Bcl I site by Eco RI cleavage, incubation with S1 nuclease, and subsequent ligation with Bcl I linkers. DNA was prepared from a positively identified colony, and the 1.9 kb XhoI-PstI fragment containing the altered restriction site was prepared via agarose gel electrophoresis. In a second modification, Bcl I-cleaved pD3 was ligated with kinased Eco RI-Bcl I adaptors (constructed from oligonucleotides ZC 525, 5'GGAATTCT3'; and ZC526, 5'GATCAGAATTCC3') in order to generate an Eco RI site as the position for inserting a gene into the expression vector. Positive colonies were identified by restriction endonuclease analysis, and DNA from this was used to isolate a 2.3 kb XhoI-PstI fragment containing the modified restriction site. The two above-described DNA fragments were incubated together with T4 DNA ligase, transformed into E. coli HB101 and positive colonies were identified by restriction analysis. A preparation of such DNA, termed pDX, was made (FIG. 12). This DNA was cleaved with Eco RI and subsequently incubated with calf-intestinal phosphatase. The purified DNA was then incubated with T4 DNA ligase and the Factor VII Eco RI fragment from pVII2463, or with the Factor VII Eco RI cDNA fragment derived from pVII2397. The resultant clones were designated FVII(2563)/pDX and FVII(565+2463)/pDX, respectively (FIG. 12). After transformation into E. coli JM83 and subsequent identification by restriction enzyme analysis, plasmid DNA preparations were made and checked by extensive restriction endonuclease digestion. The plasmids FVII(2463)/pDX and FVII(565+2463)/pDX have been deposited with American Type Culture Collection and have been assigned accession numbers Z40206, and 40205, respectively.

FVII(2463)/pDX and FVII(565+2463)/pDX (10 ug each) were each transfected, along with 10 ug salmon sperm carrier DNA, into either BHK cells or COS cells, using standard calcium-phosphate precipitation. Following transfection, the cells were cultured in the appropriate media containing 5 ug/ml vitamin K for two days. At this time, the supernatants were assayed for ELISA-positive material, using a monoclonal antibody directed against Factor VII. Both FVII(2463)/pDX and FVII(565+2463)/pDX directed the production of Factor VII polypeptide which was detected in COS cell supernatants, and Factor VII from FVII(565+2463)pDX was detected in BHK cell supernatant. Sham-transfected BHK cells or COS cells did not yield detectable levels of Factor VII (Table 5).

TABLE 5

| DNA | Cell Line | Cell Number | ELISA Positive Material (ng/ml Culture Medium) |
|---|---|---|---|
| FVII(2463)/pDX | COS | $2 \times 10^6$ | 15 |
| FVII(565 + 2463)/pDX | COS | $2 \times 10^6$ | 12 |
| Control | COS | $2 \times 10^6$ | <2 |
| FVII(2463)/pDX | BHK | $9 \times 10^6$ | 62 |
| FVII(565 + 2463)/pDX | BHK | $9 \times 10^6$ | 6 |
| Control | BHK | $9 \times 10^6$ | <2 |

FVII(2463)/pdX (10 ug) was co-transfected with 10 ug of salmon sperm DNA and 1 ug of a plasmid encoding the resistant form of dihydrofolate reductase (Simonsen and Levinson, Proc. Natl. Acad. Sci. USA 80: 2495-2499, 1983) in a mammalian expression vector, into BHK cells. After 2 days, the cells were diluted 1:20 into selective medium containing 150 nM methotrexate. The cells were fluid changed 5 days later, and colonies were isolated using cloning cylinders after an additional 5 days. Several stably transformed colonies which secreted Factor VII into the medium at approximately 20-200 ng/ml were obtained.

B. Expression of Factor VIII genomic-cDNA hybrid.

An expression vector containing genomic sequences representing the Factor VII genomic 5'-terminus and cDNA sequences from the Factor VII gene 3'-terminus was prepared as follows. Three subclones of the genomic plasmid 7 ml were used to reconstruct the 5'-terminus: 7Bam, 7SD and 7SE. Plasmid 7Bam is a 3.6 Kb EcoRI-Bam HI fragment containing exon 1a, subcloned into pCU12. A 0.7 Kb EcoRI-XbaI fragment, which contains exon 1a, was isolated from this subclone and is designated fragment a. Plasmid 7SD is a 3.7 Kb SstI fragment containing exon 1b, subcloned into pUC18. An exon 1b-containing 3.1 Kb XbaI-SstI fragment was isolated from this subclone and is designated fragment b. Plasmid 7SE is a 3.9 Kb SstI fragment containing exons 2-4, subcloned into M13mp 19. An SstI-Bgl II (0.6 Kb) fragment containing the 5' part of exon 2 was gel isolated and is designated fragment c. The remainder of the 3'-Factor VII cDNA (fragment d) was obtained as a 2 Kb BglIII-ECoRI fragment from pU-VII2463. Fragments a-d were ligated with EcoRI-cleaved and calf intestinal-phosphatased pDX, and then transformed into E. coli JM83 or HB101. Positive colonies were identified by restriction endonuclease analysis, and plasmid DNA was prepared from these colonies.

For expression Factor VII, the plasmid DNA is co-transfected into BHK or COS cells as described above. Transfected cells are cultured in vitamin K-containing medium for 2 days, and the medium is assayed for Factor VII by ELISA.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A DNA construct comprising a DNA sequence encoding Factor VII.

2. The DNA construct of claim 1 wherein at least a portion of said DNA sequence is derived from a cDNA clone of Factor VII.

3. The DNA construct of claim 1 wherein at least a portion of said DNA sequence is derived from a genomic clone of Factor VII.

4. The DNA construct of claim 1 wherein said DNA sequence comprises the cDNA sequence of FIG. 1b, from bp 36 to bp 1433.

5. The DNA construct of claim 1 wherein said DNA sequence comprises the cDNA sequence of FIG. 1b, from bp 36 to bp 99, followed downstream by the sequence from bp 166 to bp 1433.

6. A DNA construct comprising a first nucleotide sequence joined to a second nucleotide sequence positioned downstream of said first sequence, said first and second sequences derived from cDNA clones of Factor VII, the joined sequences coding for a protein which upon activation has substantially the same biological activity for blood coagulation as Factor VIIa.

7. A DNA construct comprising a first nucleotide sequence derived from a genomic clone of Factor VII, joined to a second nucleotide sequence positioned downstream of said first sequence, said second sequence derived from a cDNA clone of Factor VII, the joined sequence coding for a protein which upon activation has substantially the same biological activity for blood coagulation as Factor VIIa.

8. A recombinant plasmid comprising a DNA sequence encoding Factor VII.

9. The recombinant plasmid of claim 8 wherein the DNA sequence comprises the cDNA sequence of FIG. 1b from bp 36 to bp 1433.

10. The recombinant plasmid of claim 8 wherein the DNA sequence comprises the cDNA sequence of FIG. 1b from bp 36 to bp 99, followed downstream by the sequence from bp 166 to bp 1433.

11. The recombinant plasmid of claim 8 wherein said DNA sequence comprises Factor VII cDNA.

12. The recombinant plasmid of claim 8 wherein said DNA sequence comprises Factor VII genomic DNA.

13. A recombinant plasmid capable of integration in mammalian host cell DNA, said plasmid comprising a promoter followed downstream by a DNA sequence encoding Factor VII, said DNA sequence being followed downstream by a polyadenylation signal.

14. A recombinant plasmid capable of integration in mammalian host cell DNA, said plasmid comprising a promoter followed downstream by a first nucleotide sequence joined to a second nucleotide sequence positioned downstream of said first sequence, said first and second sequences derived from cDNA clones of Factor VII, the joined sequences coding for a protein which upon activation has substantially the same biological activity for blood coagulation as Factor VIIa, the joined sequences being followed downstream by a polyadenylation signal.

15. A recombinant plasmid capable of integration in mammalian host cell DNA, said plasmid comprising a promoter followed downstream by a first nucleotide sequence derived from a genomic clone of Factor VII, joined to a second nucleotide sequence positioned downstream of said first sequence, said second sequence derived from a cDNA clone of Factor VII, the joined sequences coding for a protein which upon activation has substantially the same biological activity for blood coagulation as Factor VIIa, the joined sequences being followed downstream by a polyadenylation signal.

16. Mammalian cells stably transfected with a recombinant plasmid comprising a DNA sequence encoding Factor VII, said cells producing Factor VII in recoverable amounts.

17. The cells of claim 16 wherein the DNA sequence comprises the cDNA sequence of FIG. 1b from bp 36 to bp 1433.

18. The cells of claim 16 wherein the DNA sequence comprises the cDNA sequence of FIG. 1b from bp 36 to bp 99, followed downstream by the sequence from bp 166 to bp 1433.

19. The cells of claim 16 wherein said DNA sequence comprises Factor VII cDNA.

20. The cells of claim 16 wherein said DNA sequence comprises Factor VII genomic DNA.

21. The cells of claim 16 wherein said plasmid comprises a promoter followed downstream by a DNA sequence encoding Factor VII, said DNA sequence being followed downstream by a polyadenylation signal.

22. The cells of claim 16 wherein said plasmid comprises a promoter followed downstream by a first nucleotide sequence joined to a second nucleotide sequence positioned downstream of said first sequence, said first and second sequences derived from cDNA clones of Factor VII, the joined sequences coding for a protein which upon activation has substantially the same biological activity for blood coagulation as Factor VIIa, the joined sequences being followed downstream by a polyadenylation signal.

23. The cells of claim 16 wherein said plasmid comprises a promoter followed downstream by a first nucleotide sequence derived from a genomic clone of Factor VII, joined to a second nucleotide sequence positioned downstream of said first sequence, said second sequence derived from a cDNA clone of Factor VII, the joined sequences coding for a protein which upon activation has substantially the same biological activity for blood coagulation as Factor VIIa, the joined sequences being followed downstream by a polyadenylation signal.

24. A method for producing a protein having biological activity for blood coagulation mediated by Factor VIIa, comprising:
   establishing a mammalian host cell which contains a DNA construct comprising a DNA sequence encoding Factor VII;
   growing said mammalian host cell in an appropriate medium;
   isolating the protein product encoded by said DNA construct produced by said mammalian host cell; and
   activating said protein product to generate Factor VIIa.

25. The method of claim 24, including amplification of the DNA sequence by cotransfection of the host cell with a gene encoding dihydrofolate reductase, wherein the appropriate medium comprises methotrexate.

26. The method of claim 24 wherein said protein product is activated by reacting the protein with a proteolytic enzyme selected from the group consisting of Factor XIIa, Factor IXa, kallikrein, Factor Xa, and thrombin.

27. The method of claim 24 wherein said DNA sequence comprises Factor VII cDNA.

28. The method of claim 24 wherein said DNA sequence comprises Factor VII genomic DNA.

29. The method of claim 24 wherein said DNA sequence comprises the cDNA sequence of FIG. 1b, from bp 36 to bp 1433.

30. The method of claim 24 wherein said DNA sequence comprises the cDNA sequence of FIG. 1b, from bp 36 to bp 99, followed downstream by the sequence from bp 166 to bp 1433.

31. The method of claim 24 wherein said DNA sequence comprises a first nucleotide sequence joined to a second nucleotide sequence positioned downstream of said first sequence, said first and second sequences derived from cDNA clones of Factor VII, the joined sequences coding for a protein which upon activation has substantially the same biological activity for blood coagulation as Factor VIIa.

32. The method of claim 24 wherein said DNA sequence comprises a first nucleotide sequence derived from a genomic clone of Factor VII, joined to a second nucleotide sequence positioned downstream of said first sequence, said second sequence derived from a cDNA clone of Factor VII, the joined sequences coding for a protein which upon activation has substantially the same biological activity for blood coagulation as Factor VIIa.

* * * * *

UNITED STATES PATENT AND TRADEMARK OFFICE
CERTIFICATE OF CORRECTION

PATENT NO. : 4,784,950

DATED : November 15, 1988

INVENTOR(S) : Frederick S. Hagen et al.

It is certified that error appears in the above-identified patent and that said Letters Patent is hereby corrected as shown below:

In the abstract, column 2, line 3, after "Factor VII", insert --or Factor IX--.

In column 5, line 31, delete "usee" and substitute therefor --used--.

In column 5, line 52, delete "FVI1" and substitute therefor --FVII--.

In column 11, line 32, after "sequence was", delete "the" and substitute therefor --then--.

In column 13, line 38, delete "pUC 13" and substitute therefor --pUC13--.

In column 15, line 17, delete "terminal" and substitute therefor --termini--.

In column 17, line 56, delete "$^{32}$p" and substitute therefor --$^{32}$P--.

In column 18, line 65, delete "AC528" and substitute therefor --ZC528--.

In column 19, line 52, delete "Rb-enriched" and substitute therefor --Kb-enriched--.

UNITED STATES PATENT AND TRADEMARK OFFICE
CERTIFICATE OF CORRECTION

PATENT NO. : 4,784,950

DATED : November 15, 1988

INVENTOR(S) : Frederick S. Hagen et al.

It is certified that error appears in the above-identified patent and that said Letters Patent is hereby corrected as shown below:

In column 21, line 63, delete "Hind II" and substitute therefor --Hind III--.

In column 22, line 1, delete "mm" and substitute therefor --mM--, line 59, delete "cDNa" and substitute therefor --cDNA--.

In column 24, line 13, delete "hybride" and substitute therefor --hybrid--.

In column 24, line 16, delete "cDNa" and substitute therefor --cDNA--.

In column 26, line 24, delete "BAM HI" and substitute therefor --Bam HI--.

In column 27, line 2, delete "BAM HI" and substitute therefor --Bam HI--.

In column 30, line 65, delete "BcL" and substitute therefor --Bcl--.

In column 31, line 33, delete "pBr 322" and substitute therefor --pBR322--, and delete "Botcham" and substitute therefor --Botchan--.

UNITED STATES PATENT AND TRADEMARK OFFICE
CERTIFICATE OF CORRECTION

PATENT NO. : 4,784,950

DATED : November 15, 1988

INVENTOR(S) : Frederick S. Hagen et al.

It is certified that error appears in the above-identified patent and that said Letters Patent is hereby corrected as shown below:

In column 31, line 35, delete "Botcham" and substitute therefor --Botchan--.
In column 32, line 23, delete "pD 3" and substitute therefor --pD3--.
In column 32, line 60, delete "7 ml" and substitute therefor --7ml--.
In column 33, line 8, delete "pUC 18" and substitute therefor --pUC18--.
In column 33, line 54, delete "Z40206" and substitute therefor --40206--.
In column 34, line 14, delete "pdX" and substitute therefor --pDX--.
In column 34, line 32, delete "7 ml" and substitute therefor --7ml--.
In column 34, line 35, delete "pCU12" and substitute therefor --pUC12--.
In column 34, line 53, after "expression" insert --of--.

Signed and Sealed this

Tenth Day of July, 1990

Attest:

HARRY F. MANBECK, JR.

Attesting Officer        Commissioner of Patents and Trademarks

UNITED STATES PATENT AND TRADEMARK OFFICE

(12)             CERTIFICATE EXTENDING PATENT TERM
                        UNDER 35 U.S.C. § 156

(68) PATENT NO.             4,784,950

(45) ISSUED                 November 15, 1988

(75) INVENTOR            Frederick S. Hagen, et al.

(73) PATENT OWNER     NOVO NORDISK HEALTH CARE AG

(95) PRODUCT            NOVOSEVEN® (rhFVIIa)

This is to certify that an application under 35 U.S.C. § 156 has been filed in the United States Patent and Trademark Office, requesting extension of the term of U.S. Patent No. 4,784,950 based upon the regulatory review of the product NOVOSEVEN® (rhFVIIa) by the Food and Drug Administration. Since it appears that the requirements of the law have been met, this certificate extends the term of the patent for the period of

(94)                     Five years from November 15, 2005, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 17th day of November 2004.

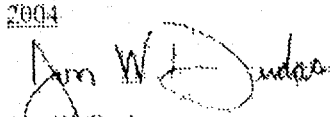

Jon W. Dudas
Under Secretary of Commerce for Intellectual Property and
Director of the United States Patent and Trademark Office